US012428424B2

(12) United States Patent
Miller

(10) Patent No.: US 12,428,424 B2
(45) **Date of Patent: *Sep. 30, 2025**

(54) ESTROGEN RECEPTOR-MODULATING COMPOUNDS

(71) Applicant: RADIUS PHARMACEUTICALS, INC., Boston, MA (US)

(72) Inventor: Chris P. Miller, San Mateo, CA (US)

(73) Assignee: RADIUS PHARMACEUTICALS, INC., Boston, MA (US)

( * ) Notice: Subject to any disclaimer, the term of this patent is extended or adjusted under 35 U.S.C. 154(b) by 863 days.

This patent is subject to a terminal disclaimer.

(21) Appl. No.: 17/629,041

(22) PCT Filed: Jul. 21, 2020

(86) PCT No.: PCT/US2020/042903

§ 371 (c)(1),
(2) Date: Jan. 21, 2022

(87) PCT Pub. No.: WO2021/016254

PCT Pub. Date: Jan. 28, 2021

(65) Prior Publication Data

US 2022/0281875 A1 Sep. 8, 2022

Related U.S. Application Data

(60) Provisional application No. 62/876,963, filed on Jul. 22, 2019.

(51) Int. Cl.

| | |
|---|---|
| ***C07D 487/04*** | (2006.01) |
| ***A61K 31/4162*** | (2006.01) |
| ***A61P 35/00*** | (2006.01) |
| ***A61P 35/02*** | (2006.01) |

(52) U.S. Cl.

CPC ............ *C07D 487/04* (2013.01); *A61P 35/00* (2018.01)

(58) Field of Classification Search

CPC ........ C07D 487/04; A61P 35/00; A61P 35/02; A61K 31/4162

See application file for complete search history.

(56) References Cited

U.S. PATENT DOCUMENTS

| | | | | |
|---|---|---|---|---|
| 5,916,916 | A | 6/1999 | Hauser | |
| 6,358,943 | B1 * | 3/2002 | Ullrich | A61K 31/4535 540/602 |
| 6,821,989 | B2 | 11/2004 | Rosati | |
| 6,844,336 | B2 | 1/2005 | Kuenzer et al. | |
| 7,138,426 | B2 | 11/2006 | DiNinno | |
| 9,187,460 | B2 | 11/2015 | Smith | |
| 11,384,068 | B2 * | 7/2022 | Miller | C07C 43/253 |
| 2003/0130276 | A1 | 7/2003 | Rosati | |

FOREIGN PATENT DOCUMENTS

| | | | | |
|---|---|---|---|---|
| EA | 000815 | B1 | 4/2000 | |
| GB | 2300857 | A * | 11/1996 | C07D 487/04 |
| WO | 9907377 | A1 | 2/1999 | |
| WO | 9915500 | A1 | 4/1999 | |
| WO | 2004032716 | A2 | 4/2004 | |
| WO | 2016097072 | A1 | 6/2016 | |
| WO | 2016189011 | A1 | 12/2016 | |
| WO | 2019144132 | A1 | 7/2019 | |

OTHER PUBLICATIONS

Paterni, I. et al. Expert Opinion on Therapeutic Patents, 2013, 23(10), 1247-1271 (Year: 2013).*

PCT/US2020/042903 International Search Report dated Sep. 15, 2020.

Denya, Ireen, et al, Indazole derivatives and their therapeutic applications: a patent review (2013-2017), Expert Opinion on Therapeutic Patents, vol. 28, No. 6 May 11, 2018, pp. 441-453, XP055726835, ISSN: 1354-3776.

China 202080051792.9 Search Report dated Aug. 1, 2023.

Russia 2022101182 Search Report dated Dec. 21, 2023.

Singapore 11202200582W Written Opinion and Search Report date Sep. 6, 2023.

Belikov, V.G., Pharmaceutical Chemistry, Moscow, High School, vol. 1, pp. 43-47, 1993.

Durnov, L.A., et al., Pediatric Oncology, Second Edition, 2002.

Dyson, G., et al., Chemistry of Synthetic Drugs, Publishing House, MIR, Moscow, 1964.

Kummerer, K., Pharmaceuticals in the Environment, The Annual Review of Environment and Resources, vol. 35, pp. 57-75, Aug. 18, 2010.

* cited by examiner

*Primary Examiner* — Clinton A Brooks
*Assistant Examiner* — Kendall Nicole Heitmeier
(74) *Attorney, Agent, or Firm* — Honigman LLP; Christopher C. Forbes

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

10 Claims, No Drawings

ESTROGEN RECEPTOR-MODULATING COMPOUNDS

CROSS-REFERENCE TO RELATED APPLICATIONS

This application is a National Stage Application and claims priority under 35 U.S.C. § 371 to Patent Cooperation Treaty application PCT/US2020/042903, filed Jul. 21, 2020, which claims the benefit of and priority under 35 U.S.C. § 119 (e) to U.S. Provisional Application No. 62/876,963, filed on Jul. 22, 2019. Priority is claimed to both of these applications and the disclosures of these prior applications are considered part of the disclosure of this application, and to the extent allowed, the entire contents of the aforementioned applications are incorporated herein.

TECHNICAL FIELD

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND

The estrogen receptor ("ER") is a ligand-activated transcriptional regulatory protein that mediates induction of a variety of biological effects through its interaction with endogenous estrogens. Endogenous estrogens include 17β-estradiol and estrone. The estrogen receptor has been found to have two isoforms, ER-α (ESR1) and ER-β (ESR2). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions, such as infertility, osteoporosis, vaginal atrophy, dyspareunia, contraception, male hypogonadism, gynecomastia, breast pain, and accordingly find use in the treatment of these and other conditions and diseases that are at least in part attributable to regulation of the estrogen receptor.

Selective estrogen receptor modulators (SERMs) are a class of drugs that act on the estrogen receptor. They tend to be competitive ligands of the estrogen receptor. A characteristic that distinguishes these substances from pure ER agonists and antagonists (that is, full agonists and silent antagonists) is that their action is different in various tissues, thereby granting the possibility to selectively inhibit or stimulate estrogen-like action in various tissues. For example, ER-α is typically found as the predominant form in the female reproductive tract and mammary glands, while ER-β is found in higher levels in vascular endothelial cells, bone, and male prostate tissue. Different tissues have different degrees of sensitivity to and activity of endogenous estrogens, so SERMs produce estrogenic or antiestrogenic effects depending on the specific tissue in question as well as the percentage of intrinsic activity (IA) of the SERM. Moreover, their levels in various tissues may change in response to physical development, aging or disease state. Antagonizing at the ER can either occur through competitive inhibition, wherein one ligand displaces a more agonistic ligand (e.g., 17β-estradiol) and signals to a lesser degree or not at all relative to the agonist ligand. There is a second mode of inhibiting ER-agonist signaling and this comprises the binding of a ligand to ER and inducing a conformation or conformations that trigger the degradation of the ER in the proteasome. Often, the degradation is triggered by ubiquination and/or palmoylation of ER subsequent to a binding event of the degradation-triggering compound. Compounds that bind ER and accelerate its degradation are often referred to as selective estrogen receptor degraders ("SERDs"). Referring to a compound as a SERM or SERD is a general way to focus on that aspect of its pharmacology. As it turns out, many compounds that function as SERMs, meaning they have at least some agonist activity in some (but not all) ER-expressing tissues, can also trigger at least some receptor degradation. Accordingly, it should be appreciated that many if not most of the compounds falling under the embodiments of this invention represent a spectrum of SERM/SERD activity. Whether SERMs, SERDs and SERM/SERDs, the compounds of the present disclosure are able to achieve the methods disclosed herein.

SUMMARY OF THE INVENTION

In one aspect, presented herein are compounds of Formulas I to VI, D-105 to D-110, or a pharmaceutically acceptable salt, solvate or prodrug thereof, that modify the effects of endogeneous estrogens acting through ER and/or trigger ER degradation, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are selective estrogen receptor degrader compounds.

In one aspect, compounds of Formulas I to VI, D-105 to D-110, or a pharmaceutically acceptable salt, solvate or prodrug thereof, are useful for the treatment of ER-related diseases or conditions including, but not limited to, ER-α dysfunction associated with cancer such as, breast cancer, lung cancer, colorectal cancer, endometrial cancer, prostate cancer, ovarian and uterine cancer, including metastatic cancers.

In one aspect, described herein are compounds of Formulas I to VI, D-105 to D-110, and pharmaceutically acceptable salts, solvates, metabolites and prodrugs thereof. Compounds described herein are estrogen receptor modulators. In some embodiments, the compound of Formulas I to VI, D-105 to D-110 is an estrogen receptor antagonist. In some embodiments, the compound of Formulas I to VI, D-105 to D-110 displays minimal estrogen receptor agonist activity. In some embodiments, in the context of treating cancers, the compound of Formulas I to VI, D-105 to D-110 may offer improved therapeutic activity characterized by complete or longer-lasting tumor regression, a lower incidence or rate of development of resistance to treatment, and/or a reduction in tumor invasiveness.

In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from the group consisting of active metabolites, tautomers, pharmaceutically acceptable solvates, pharmaceutically acceptable salts, and prodrugs of a compound of Formulas I to VI, D-105 to D-110.

In certain embodiments, the present invention describes a compound according to Formula I.

I

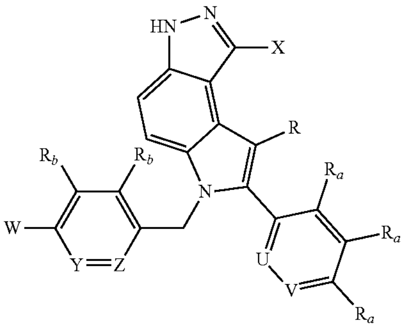

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

each $R_a$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

Y and Z are each independently selected from $CR_b$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

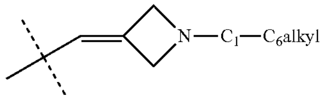

, or

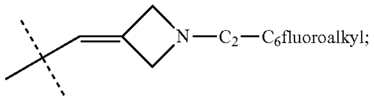

or wherein each R' is independently H or $C_1$-$C_3$ alkyl; or a pharmaceutically acceptable salt thereof.

In some embodiments of Formula I, W is —$CH_2$—$CH_2$—NH—$CH_2$—$CH_2$—$CH_3$; —$CH_2$—$CH_2$—NH—$CH_2$—$CH_2$—$CH_2F$;

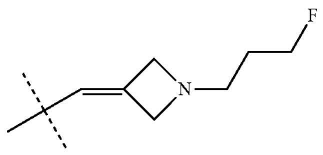

; or

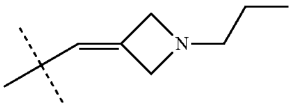

.

In some embodiments of Formula I, Y and Z are each $CR_b$ and U and V are each $CR_a$.

In some embodiments, Formula I may have a structure according to Formula II:

II

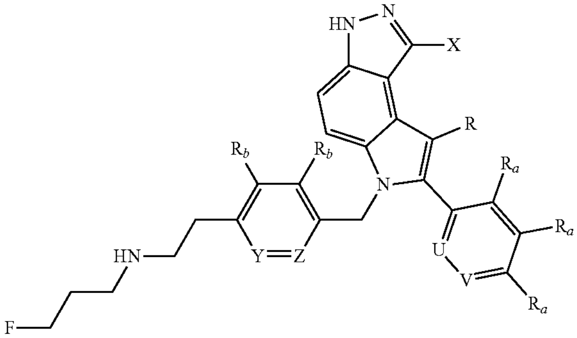

wherein

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

each $R_a$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

Y and Z are each independently selected from $CR_b$ or N; and

U and V are each independently selected from $CR_a$ or N;

or a pharmaceutically acceptable salt thereof.

In some embodiments of Formula II, X is hydrogen, methyl, fluorine, chlorine, or bromine; R is hydrogen, methyl, fluorine, chlorine, or bromine; Y and Z are each $CR_b$; U and V are each $CR_a$; each $R_a$ is independently selected from H, fluorine, or chlorine; and each $R_b$ is independently selected from H, fluorine, or chlorine; or a pharmaceutically acceptable salt thereof.

In some embodiments, Formula I and/or Formula II may have a structure according to Formula III:

III

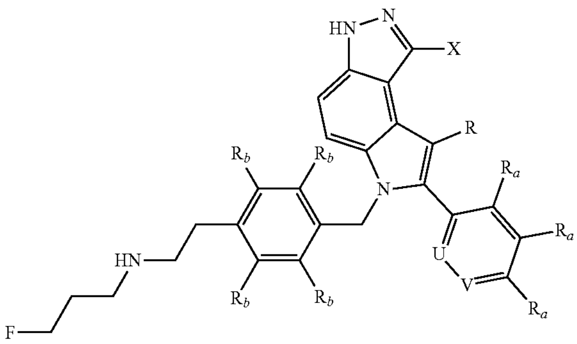

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

each $R_a$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH; and U and V are each independently selected from $CR_a$ or N;

or a pharmaceutically acceptable salt thereof.

In some embodiments of Formula III, X is hydrogen, methyl, fluorine, chlorine, or bromine; R is hydrogen, methyl, fluorine, chlorine, or bromine; U and V are each $CR_a$; each $R_a$ is independently selected from H, fluorine, or chlorine; and each $R_b$ is independently selected from H, fluorine, or chlorine.

In some embodiments of Formula III, X is fluorine and R is fluorine or chlorine.

In some embodiments, Formula I, Formula II, and/or Formula III may have a structure according to Formula IV:

IV

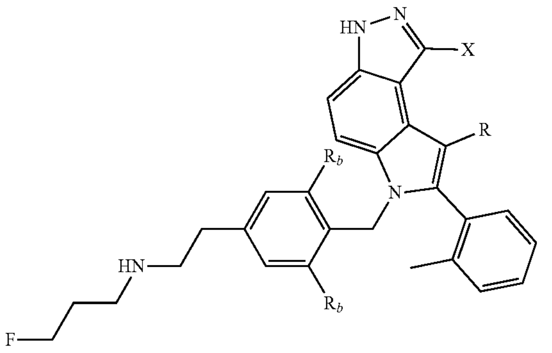

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine; and each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

or a pharmaceutically acceptable salt thereof.

In some embodiments of Formula IV, X is hydrogen or fluorine, R is hydrogen, fluorine, or chlorine, and each $R_b$ is independently hydrogen, fluorine, or chlorine.

In some embodiments, Formula I, Formula II, Formula III, and/or Formula IV may have a structure according to Formula V:

V

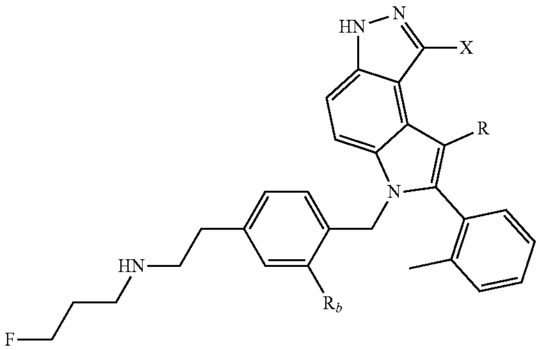

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine; and $R_b$ is selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

or a pharmaceutically acceptable salt thereof.

In some embodiments of Formula V, X is hydrogen or fluorine; R is hydrogen, fluorine, or chlorine; and $R_b$ is hydrogen, fluorine, or chlorine.

In some embodiments, Formula I, Formula II, and/or Formula III may have a structure according to Formula VI:

VI

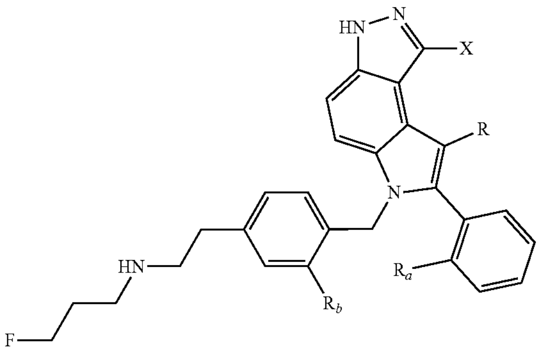

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

$R_a$ is selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH; and $R_b$ is selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

or a pharmaceutically acceptable salt thereof.

In some embodiments of Formula VI, X is hydrogen or fluorine; R is hydrogen, fluorine, or chlorine; $R_a$ is $C_1$-$C_3$ alkyl, $C_1$-$C_3$ fluoroalkyl, chlorine, or bromine; and $R_b$ is hydrogen, fluorine, or chlorine.

In some embodiments, Formula I may have a structure selected from the group consisting of:

D-105

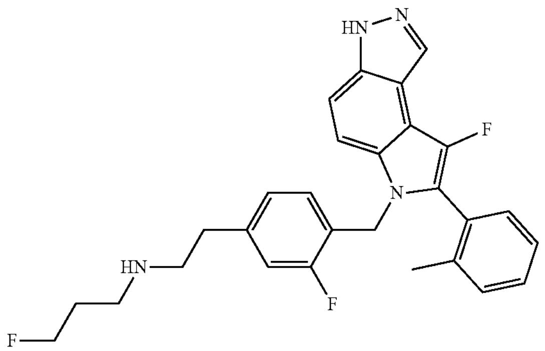

,

D-106

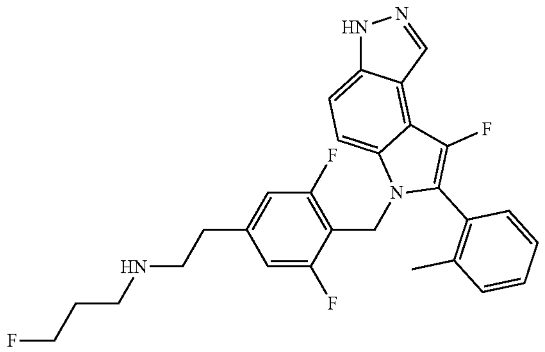

,

-continued

D-107

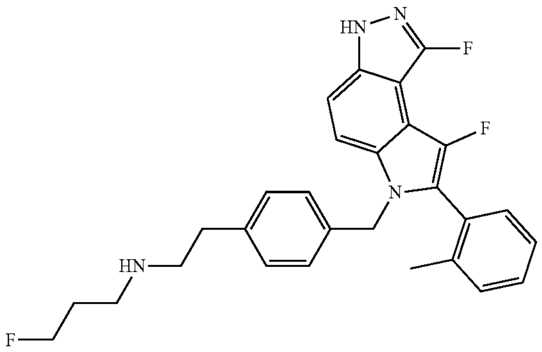

,

D-108

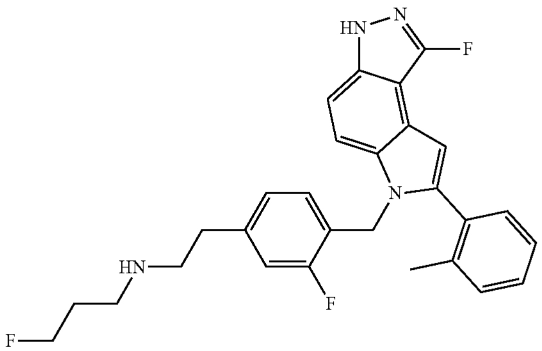

,

D-109

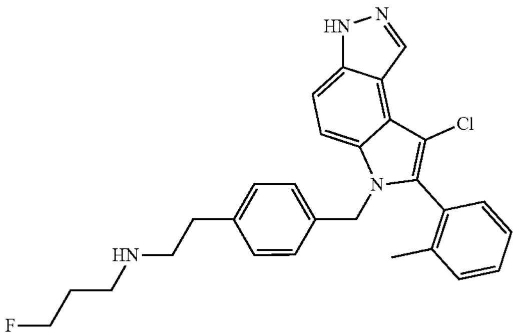

, and

D-110

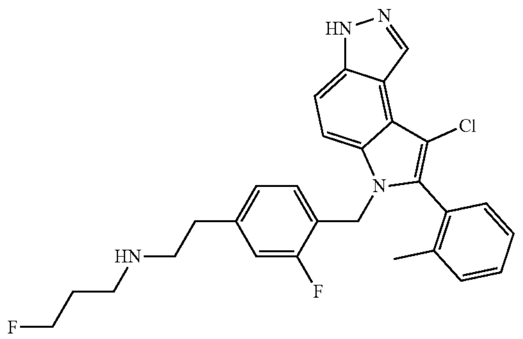

;

or a pharmaceutically acceptable salt thereof.

In certain embodiments, provided herein are pharmaceutical compositions comprising a compound selected from the group consisting of Formulas I to VI, D-105 to D-110, and all structural embodiments described herein and at least one pharmaceutically acceptable excipient.

In certain embodiments, provided herein is a method of modulating an estrogen receptor in a cell, comprising the administration of a compound to said cell wherein said compound is selected from the group consisting of Formulas I to VI, D-105 to D-110, and all the structural embodiments described herein, or a pharmaceutically acceptable salt thereof.

In certain embodiments, provided herein is a method of identifying a compound capable of modulating an estrogen receptor comprising contacting a cell expressing an estrogen receptor with a compound according to formula I, and monitoring the effect of the compound on the cell.

Also described herein is a prodrug of a compound selected from the group consisting of Formulas I to VI, D-105 to D-110, and all structural embodiments described herein. Also described herein is a pharmaceutically acceptable salt of a prodrug of a compound selected from the group consisting of Formulas I to VI, D-105 to D-110, and all structural embodiments described herein. In some embodiments, the pharmaceutically acceptable salt of the prodrug of a compound of Formulas I to VI, D-105 to D-110, is a hydrochloride salt.

In some embodiments, described herein is a pharmaceutical composition comprising a compound selected from the group consisting of Formulas I to VI, D-105 to D-110, and all structural embodiments described herein or a pharmaceutically acceptable salt or prodrug of a compound selected from the group consisting of Formulas I to VI, D-105 to D-110, and all structural embodiments described herein. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient or overabundant estrogen levels in a mammal in need thereof, wherein said method comprises the administration to said mammal of an effective amount of a compound selected from the group consisting of Formulas I to VI, D-105 to D-110, and all structural embodiments described herein or a pharmaceutically acceptable salt thereof, or a pharmaceutical composition comprising a compound of Formulas I to VI, D-105 to D-110, or one of the structural embodiments described herein, or a pharmaceutically acceptable salt thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, lung cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound selected from the group consisting of Formulas I to VI, D-105 to D-110, and all structural embodiments described herein, or a pharmaceutically acceptable salt thereof, or a pharmaceutical composition comprising a compound selected from the group consisting of Formulas I to VI, D-105 to D-110, and all structural embodiments described herein including pharmaceutically acceptable salts thereof and a pharmaceutically acceptable excipient. In some embodiments, the mammal is a human. In some embodiments, the cancer is positive for the expression of ESR1. In certain embodiments, the cancers are resistant to prior lines of treatment (e.g., prior endocrinological therapy). In certain embodiments, the cancer progresses after exposure to one or more agents selected from the group consisting of tamoxifen, toremifene, letrozole, aromasin, anastrazole, and faslodex. In some embodiments, the treatment is in adjuvant setting and in some embodiments the treatment is in the metastatic setting. In certain embodiments, SERD and/or SERMS compounds disclosed herein are combined with other active compounds including, CDK4/6 inhibitors, PI3k inhibitors, mTOR inhibitors, taxanes, HER2 inhibitors, PARP inhibitors, BCL-2 inhibitors, and MCL-1 inhibitors.

DETAILED DESCRIPTION OF THE INVENTION

As employed above and throughout the disclosure, the following terms, unless otherwise indicated, shall be understood to have the following meanings.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. The term "and/or," when used in a list of two or more items, means that any one of the listed items can be employed by itself, or any combination of two or more of the listed items can be employed. For example, if a composition is described as comprising components A, B, and/or C, the composition can contain A alone; B alone; C alone; A and B in combination; A and C in combination; B and C in combination; or A, B, and C in combination.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

In some situations, compounds may exist as tautomers. All tautomers are included within the scope of the compounds presented herein.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonism" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%. In some embodiments, a degrader as described herein lowers steady state estrogen receptor levels by at least 65%. In some embodiments, a degrader as described herein lowers steady state estrogen receptor levels by at least 85%.

The term "selective estrogen receptor degrader" or "SERD" as used herein, refers to a small molecule agent that preferentially binds to estrogen receptors versus other receptors and subsequently lowers the steady state estrogen receptor levels. In addition, SERD can mean a compound that degrades in one cell or tissue type more than in another, thus expressing possibly SERM type activity while effecting degradation differentially depending on the cellular or tissue context.

The term "Estrogen Receptor-dependent", as used herein, refers to diseases or conditions that would not occur, or would not occur to the same extent, in the absence of estrogen receptors.

The term "Estrogen Receptor-mediated", as used herein, refers to diseases or conditions that are at least in part dependent on estrogen signaling for their status.

The term "Estrogen Receptor-sensitive", as used herein, refers to diseases or conditions that would not occur, or would not occur to the same extent, in the absence of estrogens. Estrogen receptor sensitive also refers to cells or tissues that respond to the presence of estrogen receptor agonists, antagonists, SERMs and/or SERDs.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, or skin (melanoma or basal cell cancer)) or hematological tumors (such as the leukemias and lymphomas) at any stage of the disease with or without metastases.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula I to VI, and D-105 to D-110, or a pharmaceutically acceptable salt thereof, and a co-agent, are both administered to a patient simultaneously in the form of a single entity or dosage. The term "non-fixed combination" means that the active ingredients, e.g. a compound of Formula I to VI, D-105 to D-110, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some embodiments, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

In the context of this disclosure, the phrase "Formulas I through VI" "Formulas I to VI" or "Formulas I-VI" is meant to, in each instance, include compounds, for example, of Formula I, II, IIa, IIb, IIc, IId, IIe, IIf, IIg, IIh, IIj, III, IIIa, IIIb, IIIc, IIId, IIIe, IIIf, IV, IVa, IVb, IVc, IVd, IVe, IVf, IVg, IVh, IVj, V, Va, Vb, Vc, Vd, Ve, Vf, Vg, Vh, VI, VIa, VIb, VIc, VId, VIe, VIf, VIg, VIh. The same context should be applied to the phrase "D-105 to D-110" "D-105 through D-110" or "D-105-D-110" with respect to included compounds. In addition, the phrases "Formulas I through VI" "Formulas I to VI" or "Formulas I-VI", as used herein, can be interpreted as "Formula I, Formula II, Formula III, Formula IV, and/or Formula V". The phrases "D-105 to D-110" "D-105 through D-110" or "D-105-D-110", as used herein, can be interpreted as "D-105, D-106, D-107, D-108, D-109, and/or D-110".

The term "alkyl" as used herein refers to both straight and branch chain hydrocarbon radicals, having the number of carbon atoms falling within the specified range. For example, $C_{1-4}$ alkyl means that a hydrocarbon radical is attached that may contain anywhere from 1 to 4 carbon atoms with the remaining valence filled in by hydrogen atoms. The definition also includes separately each permutation as though it were separately listed. Thus, $C_{1-2}$ alkyl includes methyl and ethyl. The term $C_{1-3}$ alkyl includes methyl, ethyl, propyl and 2-propyl. The term $C_{1-4}$ alkyl includes methyl, ethyl, n-propyl, 2-propyl, n-butyl, 2-butyl, iso-butyl and tert-butyl. The term $C_{1-5}$ alkyl includes methyl, ethyl, 2-propyl, n-butyl, 2-methylbutyl, tert-butyl, n-pentyl, pentan-2-yl, pentan-3-yl, and tert-pentyl, iso-pentyl.

The term "halogen" as used herein refers to a fluorine, chlorine, bromine or iodine radical.

The term "haloalkyl" refers to an alkyl radical wherein said alkyl radical is the same as defined for the term "alkyl" except that the alkyl radical additionally has from 1 to 5 halogen atoms attached to the alkyl chain. The terms "fluoroalkyl" and "chloroalkyl", for example, refer to a haloalkyl having a single specific type of halogen such as fluorine or chlorine, respectively. In some embodiments, the haloalkyl may also include the specific halogen referenced (e.g., fluorine in fluoroalkyl) used in combination with other halogens. For example, $C_1$ haloalkyl includes $—CH_2F$, $—CHF_2$, $—CF_3$ and the like, $C_{1-2}$ haloalkyl includes $—CH_2F$, $CHF_2$, $CF_3$, $—CH_2CH_2F$, $—CH_2CHF_2$, $—CH_2CF_3$, $—CF_2CHF_2$, $—CF_2CF_3$ and the like. $C_{1-3}$ haloalkyl is defined to include $—CH_2F$, $—CHF_2$, $—CF_3$, $—CH_2CF_3$, $—CHFCF_3$, $—CF_2CF_3$, $—CHClCH_3$, $—CH_2CH_2Cl$, $—CH_2CH_2CH_2F$, $—CH_2CH_2CF_3$, and the like. $C_{1-4}$ haloalkyl is defined to include $—CH_2F$, $—CHF_2$, $—CF_3$, $—CH_2CF_3$, $—CHFCF_3$, $—CF_2CF_3$, $—CHClCH_3$, $—CH_2CH_2Cl$, $—CH_2CH_2CF_3$, $—CH_2CH_2CH_2CF_3$, $CHClCF_2CH_2CH_3$, $CF_2CH_2CH_2CHF_2$, $CH_2CH_2CH_2CH_2F$, $CH_2CH_2CH_2CH_2Cl$, and the like. The term "fluoroalkyl" as in "$C_1$-$C_4$fluoroalkyl" includes $C_1$, $C_2$, $C_3$ and $C_4$ alkyl chains, straight or branched, with from 1-4 fluorine atoms such as $—CH_2CH_2F$, $—CH_2CHF_2$, $—CH_2CF_3$, $—CF_2CHF_2$, $—CH_2F$, $—CHF_2$, $—CF_3$, $—CH_2CF_3$, $—CHFCF_3$, $—CF_2CF_3$, $—CH_2CH_2CF_3$, $CH_2CH_2CH_2F$, $—CH_2CH_2CH_2CF_3$, $CF_2CH_2CH_2CHF_2$, $CH_2CH_2CH_2CH_2F$, $CH(CH_3)CH_2F$, $CH_2(CH)(CH_3)CH_2F$, $CH_2(CH)(CH_2F)(CH_2F)$.

The term "aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

The term "acyl" refers to a group having the general formula —(CO)-alkyl wherein said alkyl radical is the same as defined for the term "alkyl" and wherein the alkyl portion of the acyl group has the number of carbon atoms falling within the specified range.

The term "acyloxy" refers to a group having the general formula —O(CO)-alkyl wherein said alkyl radical is the same as defined for the term "alkyl" and wherein the alkyl portion of the acyloxy group has the number of carbon atoms falling within the specified range.

The compounds of this invention may contain at least one stereocenter and therefore, exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R" and "S" denote the relative configurations of substituents around one or more chiral carbon atoms. When the stereochemistry of a disclosed compound is named or depicted by structure, the named or depicted stereoisomer is at least 50%, 60%, 70%, 80%, 90%, 95%, 98%, 99% or 99.9% by weight pure relative to the other stereoisomers. When a single enantiomer is named or depicted by structure, the depicted or named enantiomer is at least 50%, 60%, 70%, 80%, 90%, 95%, 98%, 99% or 99.9% by weight optically pure. Percent optical purity by weight is the ratio of the weight of the enantiomer over the weight of the enantiomer plus the weight of its optical isomer.

The compounds of the invention may be prepared as individual isomers by incorporating or starting with a specific isomer, isomer-specific synthesis, separation of diastereomers or resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Reference to a use of a compound of Formula I to VI or D-105 to D-110 or a composition that includes a compound of Formula I to VI or D-105 to D-110, wherein the compound may contain at least one stereometric center, refers to the racemate or in any optical purity of the compound of Formula I to VI or D-105 to D-110 in the composition, including but not limited to an optically pure compound.

In some embodiments, the enantiomeric ratio of the compound of Formula I to VI or D-105 to D-110 having a stereometric center is greater than 90:10. In some embodiments, the enantiomeric ratio of the compound of Formula I to VI or D-105 to D-110 is greater than 95:5. In some embodiments, the enantiomeric ratio of the compound of Formula I to VI or D-105 to D-110 is greater than 99:1. In some embodiments, the compound of Formula I to VI or D-105 to D-110 is optically pure.

Where compounds of Formula I to VI and D-105 to D-110 include one or more basic sites such as amines, acid addition salts can be made and this invention includes such acid addition salts. Some representative (non-limiting) acid addition salts include hydrochloride, hydrobromide, hydroiodide, acetate, benzenesulfonate, mesylate, besylate, benzoate, tosylate, citrate, tartrate, sulfate, bisulfate, lactate, maleate, mandelate, valerate, laurate, caprylate, propionate, succinate, phosphate, salicylate, napsylate, nitrate, tannate, resorcinate and the like, including multiprotic salts as well as mixtures of the acid addition salts. In cases where an amine is present, this invention also embraces quaternized ammonium salts of those amines. Likewise, where compounds of this invention include one or more acid sites such as carboxylic acids, phenols and the like, basic addition salts can be made and this invention includes such basic addition salts. For example, some representative (non-limiting) acidic compounds of this invention may be present as their lithium, sodium, potassium, ammonium, trialkylammonium, calcium, magnesium, barium and the like.

The compounds of this invention can also be present as solvates and such solvates are embraced within the scope of this invention even where not explicitly described. Such solvates are preferably hydrates but can be solvates comprised of other solvents, preferably where those solvents are considered to be non-toxic or at least acceptable for administration to mammals, preferably humans. The solvates can be stoichiometric or non-stoichiometric, singular or in combination. Some exemplary solvates include water, ethanol, acetic acid and the like.

The compounds of this invention, when used as therapeutics can be administered by any method known to one of skill in the art such as orally, bucally, intravenously, subcutaneously, intramuscularly, transdermally, intradermally, intravascularly, intranasally, sublingually, intracranially, rectally, intratumorally, intravaginally, intraperitonealy, pulmonary, ocularly and intratumorally.

When administered, the compounds and compositions of this invention can be provided, dosed, and/or given once daily or with multiple daily doses such as twice per day, three times per day and four times per day.

In some embodiments of this invention, the compound is administered orally where it can be formulated for solid dosage administration or liquid dosage administration. Solid dosage administration can be in the form of a tablet, granule, capsule, pill, pellet, powder and the like. Liquid dosage formulations include syrups, solutions, gels, suspensions, elixirs, emulsions, colloids, oils, and the like.

In some embodiments, the compounds of the present invention can include solids where the solid compounds can be defined using particle size. Where the compound of this invention is not particularly water soluble, it is sometimes preferable to administer the compound with a certain particle size. In some embodiments, the solids comprising the compound of Formulas I to VI and D-105 to D110 can have an average mean particle size diameter of under 100 microns, or under 75 microns, or under 50 microns, or under 35 microns, or under 10 microns or under 5 microns.

Solid dosage formulations will comprise at least one compound of this invention together with one or more pharmaceutical excipients.

The solid dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

The compounds of this invention may be employed alone or in combination with other therapeutic agents. By way of non-limiting example, the compounds of this invention can be used in combination with one or more of a cdk4/6 inhibitor, PI3K inhibitor, mTOR inhibitor, and a taxane. In some embodiments of this invention, the compounds of this invention can be used in combination with an m-TOR inhibitor selected from the group consisting of sirolimus, temsirolimus, everolimus, and ridafarolimus; an CDK4/6 inhibitor selected from the group consisting of abemaciclib, ribociclib, and palbociclib; a PI3k inhibitor; a PARP inhibitor; a BCL-2 inhibitor; a MCL-1 inhibitor; and any combinations thereof.

The compounds of this invention may be administered according to different dosage scheduling and the dosage may be adjusted as deemed necessary by the subject or preferably by the subject in consultation with a qualified practitioner of medicine. Dosing of the compounds of this invention can take place by multiple routes and consequently, the dosing schedule and amounts are dependent not only on the particular subject's weight, sex, age, therapy contemplated, etc. but also by the route of the drug chosen.

By way of non-limiting example, the compounds of this invention may be considered for dosing by the oral route with optimal efficacy and/or safety being the goal.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc. In some embodiments, a compound is dosed once every seven days.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient or overabundant estrogen levels in a mammal in need thereof, wherein said method comprises the administration to said mammal of an effective amount of a compound selected from the group consisting of Formulas I to VI, D-105 to D-110, and all structural embodiments described herein or a pharmaceutically acceptable salt thereof, or a pharmaceutical composition comprising a compound of Formulas I to VI, D-105 to D-110, or one of the structural embodiments described herein, or a pharmaceutically acceptable salt thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, lung cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound selected from the group consisting of Formulas I to VI, D-105 to D-110, and all structural embodiments described herein, or a pharmaceutically acceptable salt thereof, or a pharmaceutical composition comprising a compound selected from the group consisting of Formulas I to VI, D-105 to D-110, and all structural embodiments described herein including pharmaceutically acceptable salts thereof and a pharmaceutically acceptable excipient. In an embodiment, the mammal is a human. In some embodiments, the cancer is positive for the expression of ESR1. In certain embodiments, the cancers are resistant to prior lines of treatment (e.g., prior endocrinological therapy). In certain embodiments, the cancer progresses after exposure to one or more agents selected from the group consisting of tamoxifen, toremifene, letrozole, aromasin, anastrazole, and faslodex. In some embodiments, the treatment is in adjuvant setting and in some embodiments the treatment is in the metastatic setting. In certain embodiments, SERD and/or SERM compounds disclosed herein are combined with other active compounds including, CDK4/6 inhibitors, PI3k inhibitors, mTOR inhibitors, taxanes, HER2 inhibitors, PARP inhibitors, BCL-2 inhibitors, and MCL-1 inhibitors.

Also provided herein is a method of inhibiting tumor growth or producing tumor regression in a subject having an estrogen receptor alpha-positive cancer comprising administering to said subject a therapeutically effective amount of a compound of Formulas I to VI or D-105 to D-110 or a pharmaceutically acceptable salt, solvate or prodrug thereof. In some embodiments, the estrogen receptor alpha-positive cancer is a drug-resistant estrogen receptor alpha-positive cancer. In some embodiments, the cancer is selected from breast cancer, uterine cancer, ovarian cancer, and pituitary cancer. In some embodiments, the cancer is breast cancer. In some embodiments, the cancer is metastatic. In some embodiments, the cancer is positive for the mutant estrogen receptor alpha comprising one or more mutations selected from the group consisting of Y537$X_1$ (wherein $X_1$ is S, N, or C), L536$X_2$ (wherein $X_2$ is R or Q), P535H, V534E, S463P, V392I, E380Q, D538G, and combinations thereof. In some embodiments, the mutation is Y537S. In some embodiments, the subject has osteoporosis or a high risk of osteoporosis. In some embodiments, the subject is a pre-menopausal woman. In some embodiments, the subject is a post-menopausal woman who had relapsed or progressed after previous treatment with SERMs, CDK inhibitors, and/or AIs. In some embodiments, the tumor is resistant to a drug selected from the group consisting of anti-estrogens (e.g., tamoxifen or fulvestrant), aromatase inhibitors (e.g., aromasin), CDK inhibitors (e.g., abemaciclib, ribociclib, or palbociclib), and combinations thereof. In some embodiments, the therapeutically effective amount of a compound of Formulas I to VI or D-105 to D-110 or a pharmaceutically acceptable salt, solvate or prodrug thereof is employed in combination with one or more of an anti-estrogen, an aromatase inhibitor, a CDK inhibitor, a PI3K inhibitor, an mTOR inhibitor, a taxane, a PARP inhibitor, a BCL-2 inhibitor, and a MCL-1 inhibitor.

Also provided herein is a method of inhibiting tumor growth or producing tumor regression in a subject having a mutant estrogen receptor alpha positive-cancer comprising administering to said subject a therapeutically effective amount of a compound of Formulas I to VI or D-105 to D-110 or a pharmaceutically acceptable salt, solvate or prodrug thereof. In some embodiments, the cancer is selected from breast cancer, uterine cancer, ovarian cancer, and pituitary cancer. In some embodiments, the cancer is breast cancer. In some embodiments, the cancer is metastatic. In some embodiments, the cancer is positive for the mutant estrogen receptor alpha comprising one or more mutations selected from the group consisting of Y537$X_1$ (wherein $X_1$ is S, N, or C), L536$X_2$ (wherein $X_2$ is R or Q), P535H, V534E, S463P, V392I, E380Q, D538G, and combinations thereof. In some embodiments, the mutation is Y537S. In some embodiments, the subject has osteoporosis or a high risk of osteoporosis. In some embodiments, the subject is a pre-menopausal woman. In some embodiments, the subject is a post-menopausal woman who had relapsed or progressed after previous treatment with SERMs, CDK inhibitors, and/or AIs. In some embodiments, the tumor is resistant to a drug selected from the group consisting of anti-estrogens (e.g., tamoxifen or fulvestrant), aromatase inhibitors (e.g., aromasin), CDK inhibitors (e.g., abemaciclib, ribociclib, or palbociclib), and combinations thereof. In some embodiments, the therapeutically effective amount of a compound of Formulas I to VI or D-105 to D-110 or a pharmaceutically acceptable salt, solvate or prodrug thereof is employed in combination with one or more of an anti-estrogen, an aromatase inhibitor, a CDK inhibitor, a PI3K inhibitor, an mTOR inhibitor, a taxane, a PARP inhibitor, a BCL-2 inhibitor, and a MCL-1 inhibitor.

Also provided herein is a method of treating breast cancer in a subject having a drug-resistant estrogen receptor alpha-positive cancer comprising administering to said subject a therapeutically effective amount of a compound of Formulas I to VI or D-105 to D-110 or a pharmaceutically acceptable salt, solvate or prodrug thereof. In some embodiments, the drug resistant breast cancer is resistant to one or more antiestrogens (e.g., tamoxifen, toremifene, fulvestrant), CDK inhibitors (e.g., abemaciclib, ribociclib, or palbociclib), and/or aromatase inhibitors (e.g., aromasin, letrozole, anastrozole). In some embodiments, the therapeutically effective amount of a compound of Formulas I to VI or D-105 to D-110 or a pharmaceutically acceptable salt, solvate or prodrug thereof is employed in combination with one or more of an anti-estrogen, an aromatase inhibitor, a CDK inhibitor, a PI3K inhibitor, an mTOR inhibitor, a taxane, a PARP inhibitor, a BCL-2 inhibitor, and a MCL-1 inhibitor. In some embodiments, the subject expresses at least one mutant estrogen receptor alpha selected from D538G, Y537S, Y537N, Y537C, E380Q, S463P, L536R, L536Q, P535H, V392I and V534E. In some embodiments, the mutant estrogen receptor alpha is selected from Y537S, Y537N, Y537C, D538G, L536R, S463P and E380Q. In some embodiments, the mutant receptor alpha is Y537S. In some embodiments, the subject is a post-menopausal woman. In some embodiments, the subject is first identified for treatment through measuring for increased expression of one or more genes selected from ABL1, AKT1, AKT2, ALK, APC, AR, ARID1A, ASXL1, ATM, AURKA, BAP, BAP1, BCL2L11, BCR, BRAF, BRCA1, BRCA2, CCND1, CCND2, CCND3, CCNE1, CDH1, CDK4, CDK6, CDK8, CDKN1A, CDKN1B, CDKN2A, CDKN2B, CEBPA, CTNNB1, DDR2, DNMT3A, E2F3, EGFR, EML4, EPHB2, ERBB2, ERBB3, ESR1, EWSR1, FBXW7, FGF4, FGFR1, FGFR2, FGFR3, FLT3, FRS2, HIF1A, HRAS, IDH1, IDH2, IGF1R, JAK2, KDM6A, KDR, KIF5B, KIT, KRAS, LRP1B, MAP2K1, MAP2K4, MCL1, MDM2, MDM4, MET, MGMT, MLL, MPL, MSH6, MTOR, MYC, NF1, NF2, NKX2-1, NOTCH1, NPM, NRAS, PDGFRA, PIK3CA, PIK3R1, PML, PTEN, PTPRD, RARA, RB1, RET, RICTOR, ROS1, RPTOR, RUNX1, SMAD4, SMARCA4, SOX2, STK11, TET2, TP53, TSC1, TSC2, and VHL. In some embodiments, the one or more genes are selected from AKT1, AKT2, BRAF, CDK4, CDK6, PIK3CA, PIK3R1 and MTOR.

The compounds of this invention can be prepared by a variety of synthetic routes and techniques known to those of skill in the art. The processes disclosed herein should not be construed as limiting the examples or scope of the invention in any way but rather are provided as just some of the representative ways that the compounds of this invention can be or were prepared.

In some cases, protective groups are employed in the synthesis of the compounds of this invention and it should be appreciated that there are a diverse array of protective groups and strategies that can be employed in organic synthesis (T. W. Green and P. G. M. Wuts (2006) Greene's Protective Groups in Organic Synthesis, herein incorporated by reference in its entirety) and that where a protective group is referred to generically, any appropriate protective group should be considered.

In some instances, leaving groups are employed in the synthesis of compounds of this invention. Where a specific leaving group is referred to, it should be appreciated that other leaving groups might also be used. Leaving groups typically include those groups that can stabilize an anion. In the case of nucleophilic aromatic substitutions, the leaving group may be an anion or a neutrally charged group. In some cases, the leaving group for nucleophilic aromatic substitution may be a group that is not typically considered to be a stabilized anion (e.g. fluoride or hydride). While not intending to be bound by theory or the examples, some typical nucleophilic leaving groups include halogens, sulfonates (O-mesylates, O-tosylates, etc.), hydrides, quaternized amines, nitro, and the like. Additional discussion and examples can be found in leading textbooks on organic chemistry including, for example, March's Advanced Organic Chemistry: Reactions, Mechanisms, and Structure, 5th Edition, which is herein incorporated by reference in its entirety.

When any variable occurs more than one time in any constituent or in any formula, its definition in each occurrence is independent of its definition at every other occurrence. Combinations of substituents and/or variables are permissible only if such combinations result in stable compounds.

Accordingly, in some embodiments, the present invention provides novel pharmaceutically active compounds or pharmaceutical salts thereof of Formula I:

I

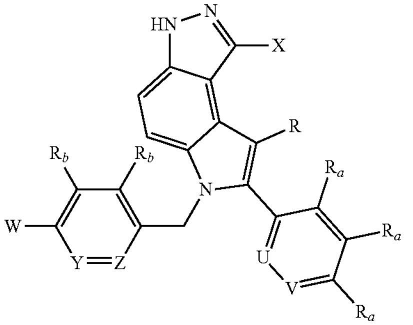

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

each $R_a$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

Y and Z are each independently selected from $CR_b$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

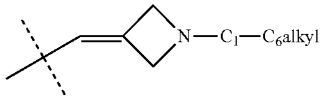

, or

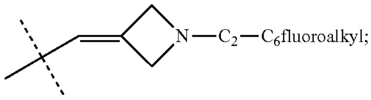

wherein each R' is independently H or $C_1$-$C_3$alkyl;

or a pharmaceutically acceptable salt thereof.

In certain embodiments, the compound of Formula I is the compound. In other embodiments, it is a pharmaceutically acceptable salt thereof.

In certain embodiments, the compound of Formula I is a pharmaceutically acceptable salt, solvate or prodrug thereof.

In certain embodiments, the pharmaceutically acceptable salt of the compound of Formula I is an acid addition salt.

In certain embodiments, the compound of Formula I is a prodrug. In yet other embodiments, the compound of Formula I is the pharmaceutically acceptable salt of the prodrug. In some aspects the pharmaceutically acceptable salt of the prodrug of a compound of Formula I is a hydrochloride salt.

In certain embodiments, a pharmaceutical composition comprising a compound or a pharmaceutically acceptable salt or prodrug of a compound of Formula I is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In certain embodiments of Formula I, W is —$CH_2$—$CH_2$—NH—$CH_2$—$CH_2$—$CH_3$; —$CH_2$—$CH_2$—NH—$CH_2$—$CH_2$—$CH_2$F;

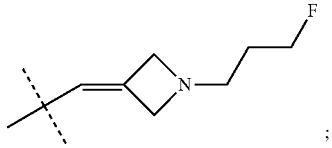

; or

-continued

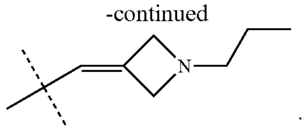

In certain embodiments of Formula I, Y and Z are each $CR_b$.

In certain embodiments of Formula I, U and V are each $CR_a$.

In some embodiments, the present invention describes compounds or pharmaceutical salts thereof of Formula I having the structure according to Formula II:

II

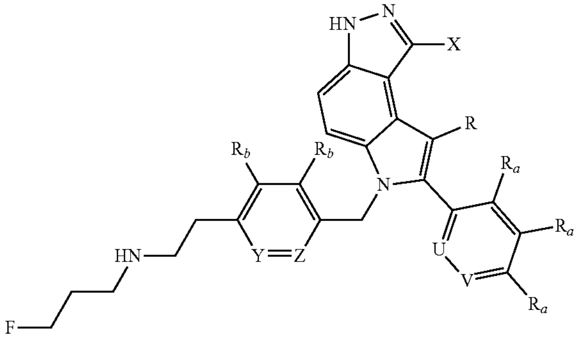

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine; each $R_a$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

Y and Z are each independently selected from $CR_b$ or N; and

U and V are each independently selected from $CR_a$ or N;

or a pharmaceutically acceptable salt thereof.

In certain embodiments of Formula II, X is hydrogen, methyl, fluorine, chlorine, or bromine.

In certain embodiments of Formula II, R is hydrogen, methyl, fluorine, chlorine, or bromine.

In certain embodiments of Formula II, Y and Z are each $CR_b$, wherein each $R_b$ is independently selected from H, fluorine, or chlorine.

In certain embodiments of Formula II, U and V are each $CR_a$ wherein each $R_a$ is independently selected from H, fluorine, or chlorine.

In some embodiments, the present invention describes compounds or pharmaceutical salts thereof of Formula I having the structure according to Formula III:

III

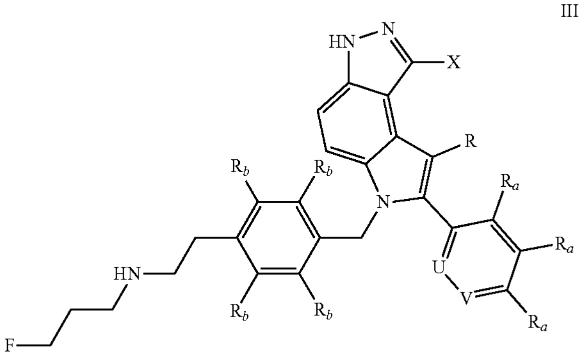

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

each $R_a$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH; and U and V are each independently selected from $CR_a$ or N;

or a pharmaceutically acceptable salt thereof.

In some embodiments of Formula III, X is hydrogen, methyl, fluorine, chlorine, or bromine; R is hydrogen, methyl, fluorine, chlorine, or bromine; U and V are each $CR_a$; each $R_a$ is independently selected from H, fluorine, or chlorine; and each $R_b$ is independently selected from H, fluorine, or chlorine.

In some embodiments of Formula III, X is fluorine and/or R is fluorine or chlorine.

In some embodiments, the present invention describes compounds or pharmaceutical salts thereof of Formula I having the structure according to Formula IV:

IV

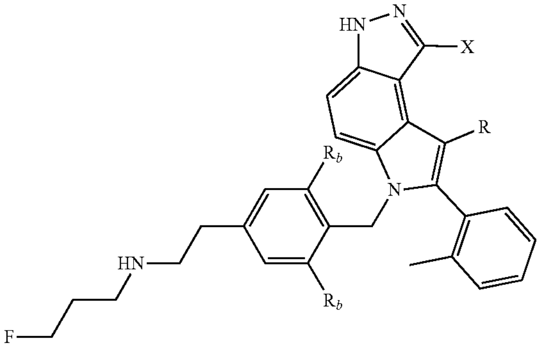

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine; and each $R_b$ is independently selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

or a pharmaceutically acceptable salt thereof.

In some embodiments of Formula IV, X is hydrogen or fluorine, R is hydrogen, fluorine, or chlorine, and/or each $R_b$ is independently selected from hydrogen, fluorine, or chlorine.

In some embodiments, the present invention describes compounds or pharmaceutical salts thereof of Formula I having the structure according to Formula V:

VI

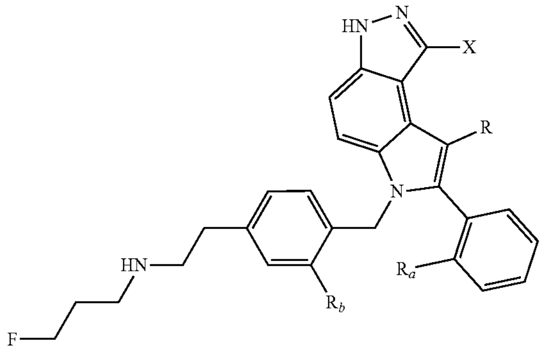

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine; and $R_b$ is selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

or a pharmaceutically acceptable salt thereof.

In some embodiments of Formula V, X is hydrogen or fluorine; R is hydrogen, fluorine, or chlorine; and/or $R_b$ is hydrogen, fluorine, or chlorine.

In some embodiments, the present invention describes compounds or pharmaceutical salts thereof of Formula I having the structure according to Formula VI:

VI

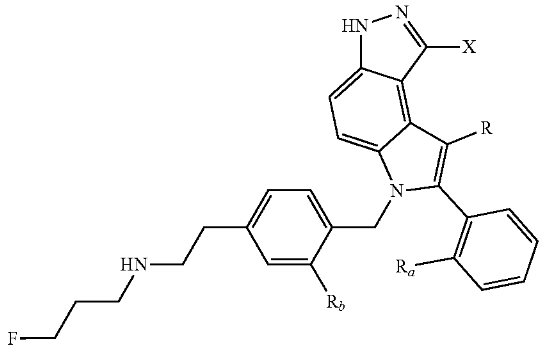

wherein:

X is hydrogen, $C_1$-$C_3$ alkyl, $C_1$-$C_3$ fluoroalkyl, CN, fluorine, chlorine, or bromine;

R is hydrogen, $C_1$-$C_3$ alkyl, $C_1$-$C_3$ fluoroalkyl, CN, fluorine, chlorine, or bromine;

$R_a$ is selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

$R_b$ is selected from: H, $C_1$-$C_3$ alkyl, $C_1$-$C_3$ fluoroalkyl, OH, $OC_{1-3}$alkyl, CN, fluorine, chlorine, or a phenyl optionally substituted with 1-3 groups selected from fluorine, chlorine, $C_1$-$C_3$ alkyl, CN, $OC_1$-$C_3$ alkyl, and OH;

or a pharmaceutically acceptable salt thereof.

In some embodiments of Formula VI, R is chlorine and $R_b$ is fluorine.

In some embodiments of Formula VI, R and $R_b$ is fluorine.

In some embodiments of Formula VI, $R_a$ is methyl, $CF_3$, or chlorine.

In some embodiments of Formula VI, X is hydrogen or fluorine; R is hydrogen, fluorine, or chlorine; $R_a$=$C_1$-$C_3$ alkyl, $C_1$-$C_3$ fluoroalkyl, chlorine or bromine; and/or $R_b$ is hydrogen, fluorine, or chlorine.

In some embodiments, the present invention describes compounds or pharmaceutical salts thereof of Formula I having a structure selected form the group consisting of:

D-105

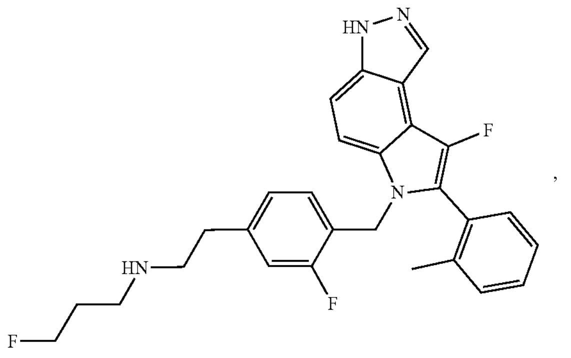

,

D-106

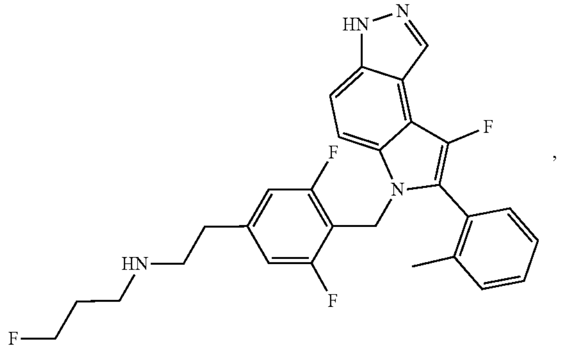

,

-continued

D-107

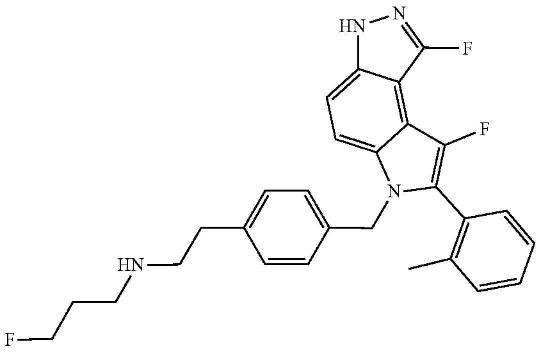

,

D-108

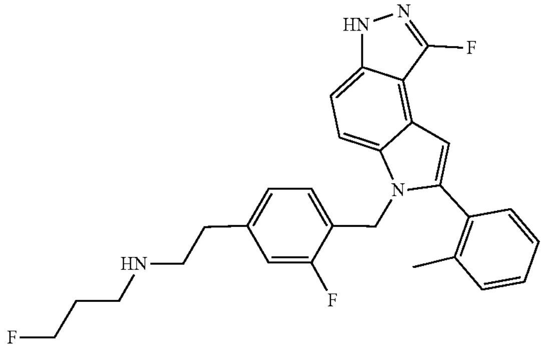

,

D-109

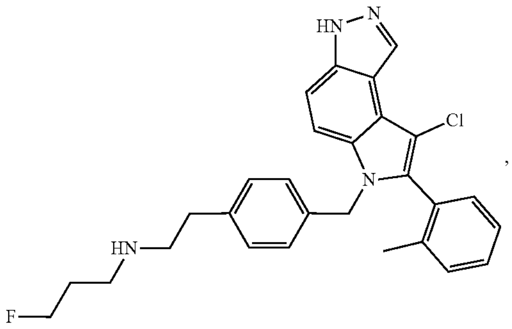

, and

D-110

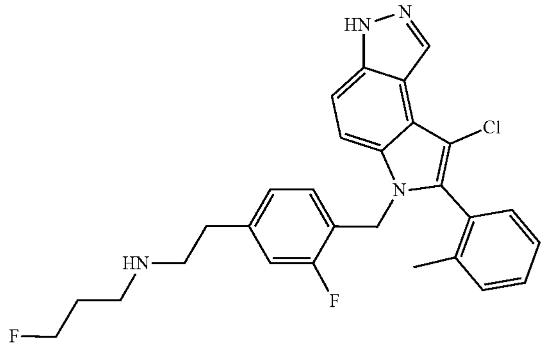

;

or a pharmaceutically acceptable salt thereof.

In some embodiments, the present invention describes compounds or pharmaceutical salts thereof of Formula I that may be selected form the group consisting of N-(4-((8-Chloro-7-(o-tolyl)pyrrolo[3,2-e]indazol-6(3H)-yl)methyl)phenethyl)-3-fluoropropan-1-amine; 3-Fluoro-N-(3-fluoro-4-((1-fluoro-7-(o-tolyl)pyrrolo[3,2-e]indazol-6(3H)-yl)methyl)phenethyl)propan-1-amine; N-(4-((1,8-difluoro-7-(o-tolyl)pyrrolo[3,2-e]indazol-6(3H)-yl)methyl)phenethyl)-3-fluoropropan-1-amine; N-(3,5-difluoro-4-((8-fluoro-7-(o-tolyl)pyrrolo[3,2-e]indazol-6(3H)-yl)methyl)phenethyl)-3-fluoropropan-1-amine; 3-fluoro-N-(3-fluoro-4-((8-fluoro-7-(o-tolyl)pyrrolo[3,2-e]indazol-6(3H)-yl)methyl)phenethyl)propan-1-amine; and N-(4-((8-chloro-7-(o-tolyl)pyrrolo[3,2-e]indazol-6(3H)-yl)methyl)-3-fluorophenethyl)-3-fluoropropan-1-amine.

In certain embodiments, provided herein are pharmaceutical compositions comprising a compound selected from the group consisting of Formulas I to VI, D-105 to D-110, and all structural embodiments described herein and at least one pharmaceutically acceptable excipient.

In some embodiments of compounds of Formulas I to VI and D-105 to D-110, the enantiomeric ratio of the compound is greater than 95:5. In some embodiments, the enantiomeric ratio of the compound is greater than 99:1.

Articles of manufacture, which include: packaging material; a compound of Formula I to VI, D-105 through D-110, or a pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Compounds described herein are synthesized using standard synthetic techniques or using methods known in the art in combination with methods described herein. In additions, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999). General methods for the preparation of compounds can be modified by the use of appropriate reagents and conditions for the introduction of the various moieties found in the formulae as provided herein.

In some embodiments, the compounds described herein are prepared as outlined in the following Schemes.
Scheme I
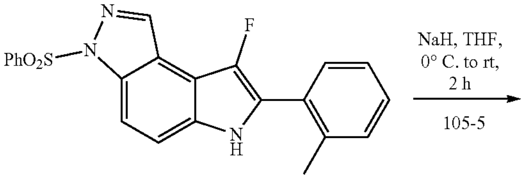
85-7
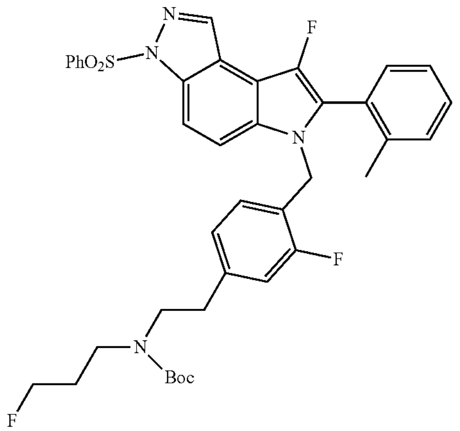
105-6
+
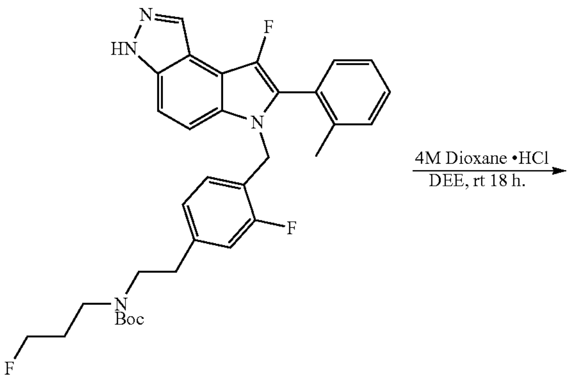
105-7
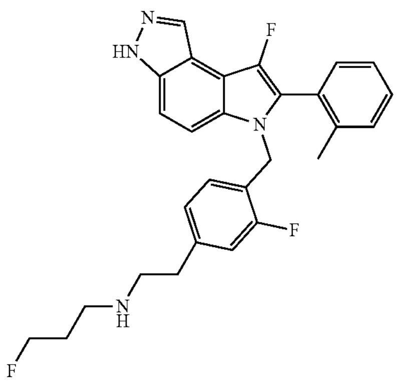
D-105
-continued
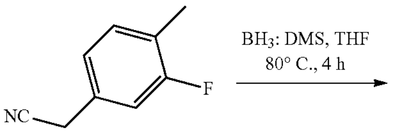
105-1
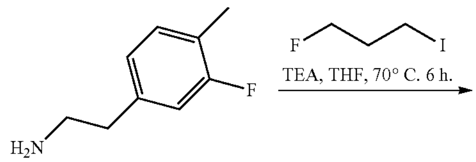
105-2
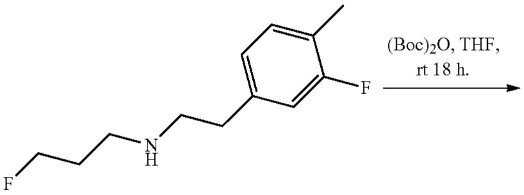
105-3
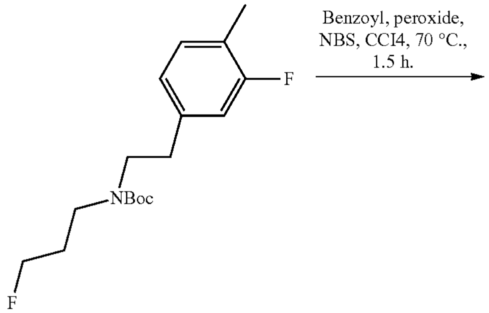
105-4
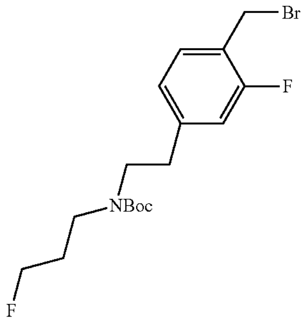
105-5
Referring to Scheme I, compound 85-7 was alkylated with the side chain 105-5 (prepared as shown) and gave a mixture of 105-6 and 105-7. The major product, compound 105-7, was treated with HCl to deprotect the secondary amine yielding D-105.

Scheme II
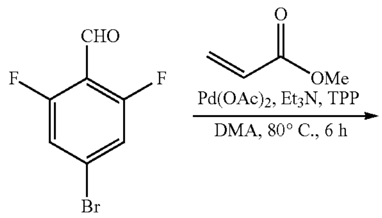
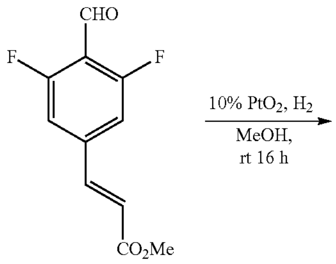
106-1
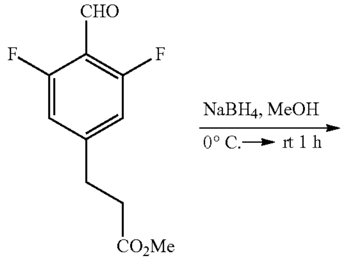
106-2
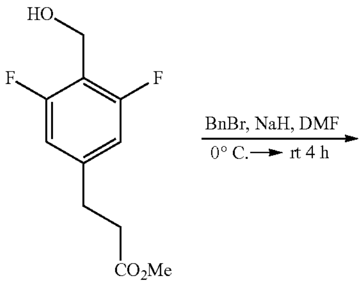
106-3
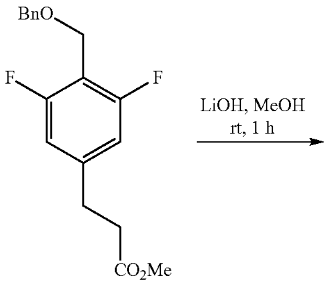
106-4
-continued
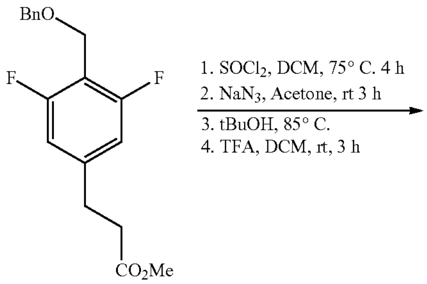
106-5
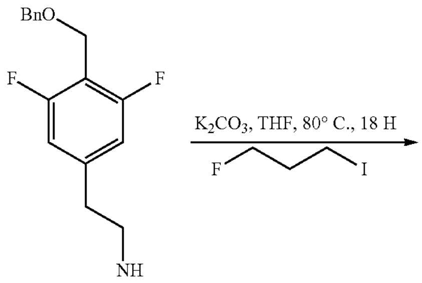
106-6
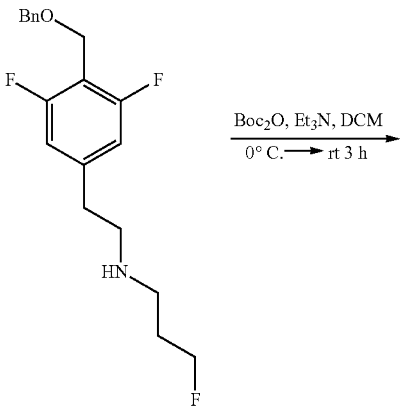
106-7
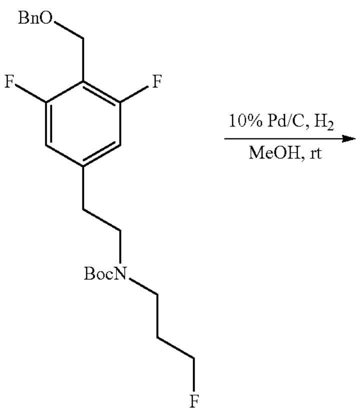
106-8

-continued
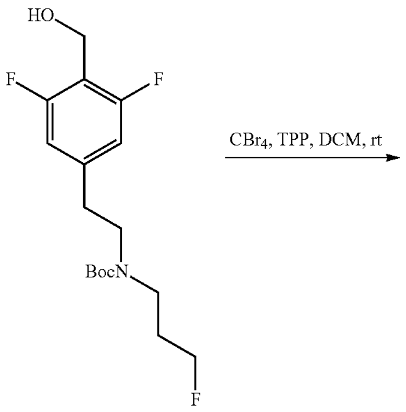
106-9
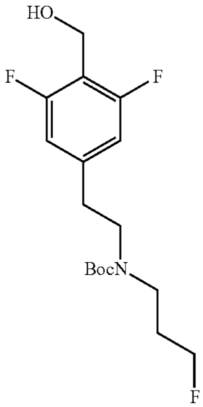
106-10
+
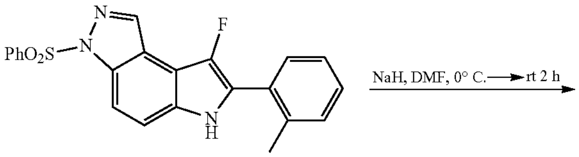
85-7
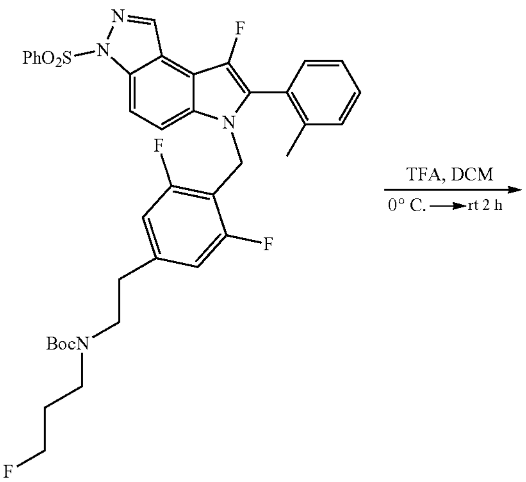
106-11
-continued
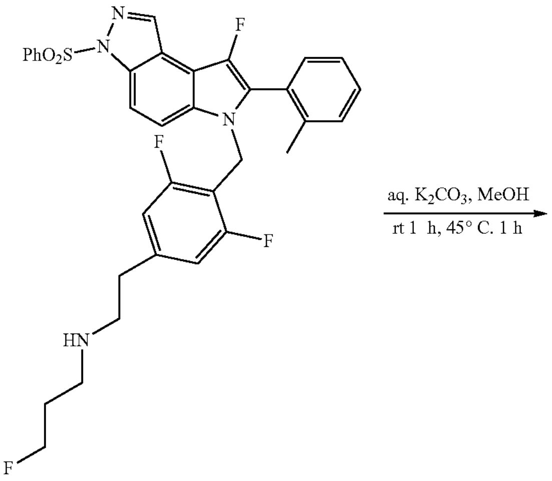
106-12
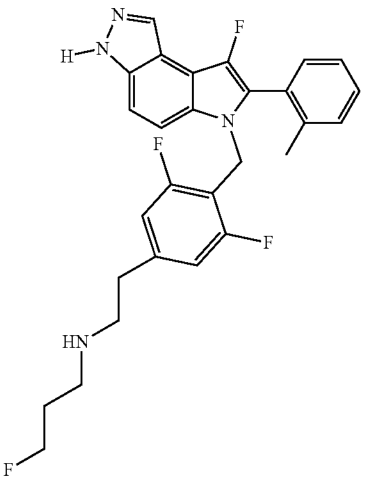
D-106
Intermediate 85-7 was alkylated with 106-10 (as prepared in Scheme II) to yield 106-11 and the secondary amine subsequently deprotected with TFA to yield 106-12 which was treated with base in aqueous methanol to yield D-106.
Scheme III
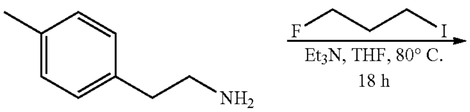
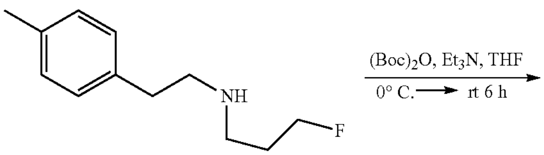
107-1

-continued
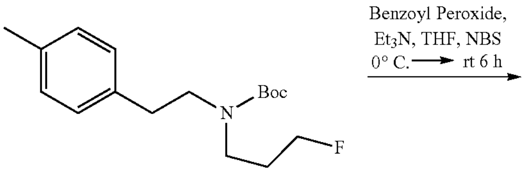
107-2
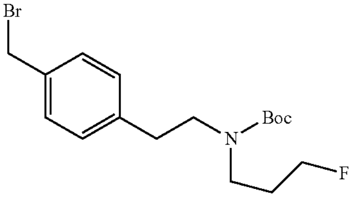
107-3
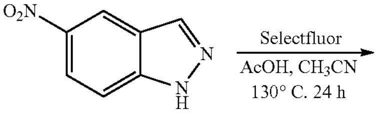
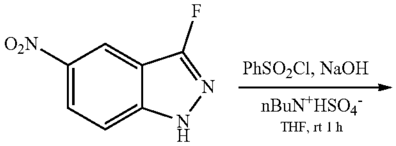
107-4
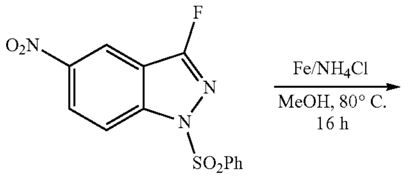
107-5
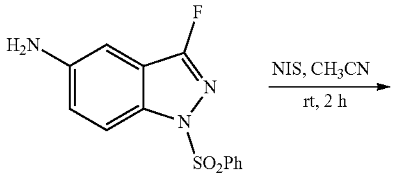
107-6
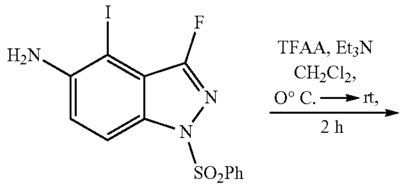
107-7
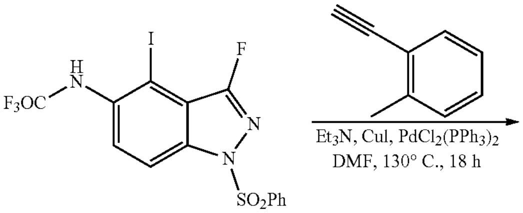
107-8
-continued
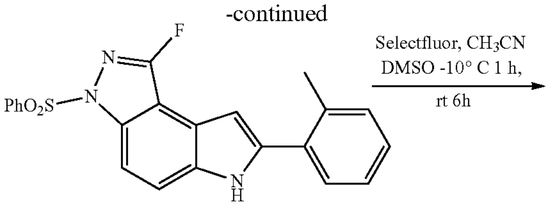
107-9
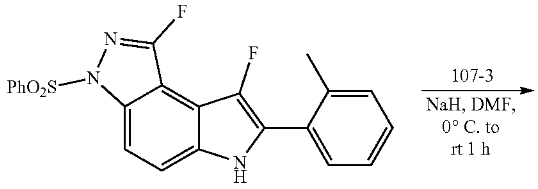
107-10
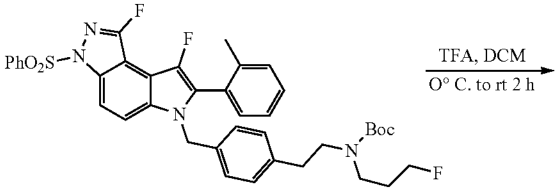
107-11
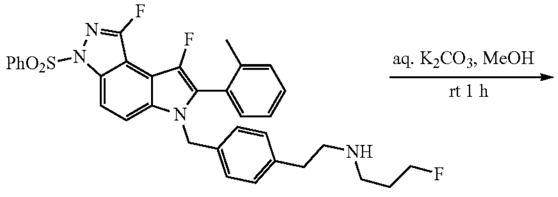
107-12
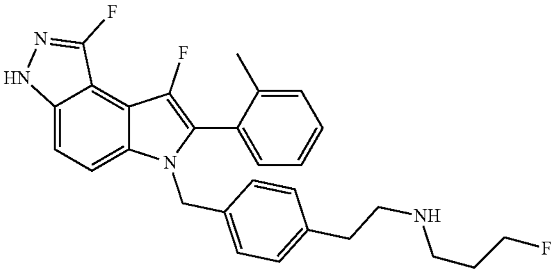
D-107
Sidechain 107-3 was prepared as provided in Scheme III and reacted with the difluorinated scaffold 107-10 (prepared as shown) in the presence of NaH to render the deprotected intermediate 107-11 which was subsequently deprotected by TFA to yield 107-12 and then subjected to base hydrolysis/methanolysis to yield the desired product D-107.
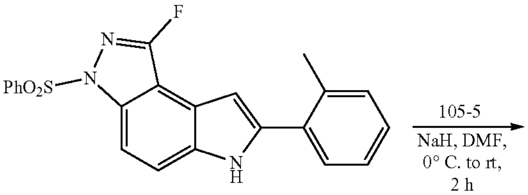
107-9

-continued
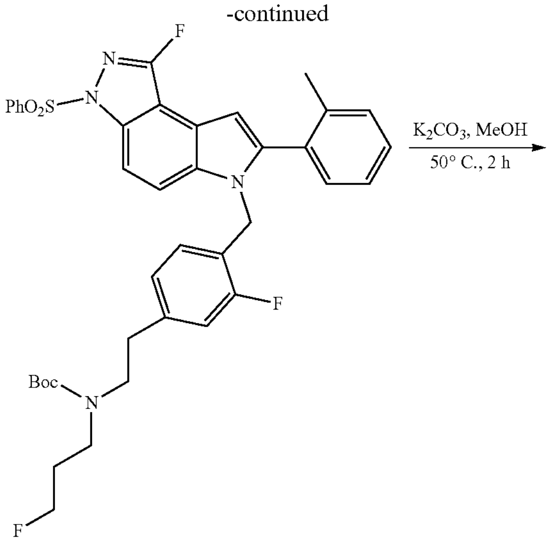
108-1
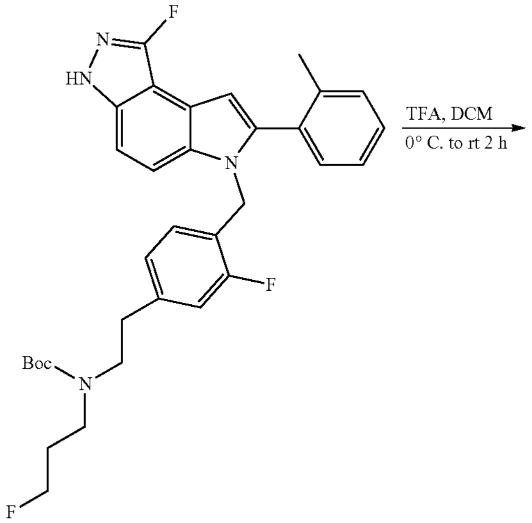
108-2
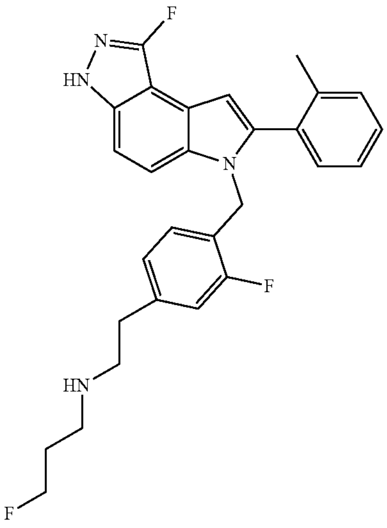
D-108
Referring now to Scheme IV, scaffold 107-9 was alkylated with sidechain 105-5 to render the intermediate 108-1, which was subsequently deprotected, first by base methanolysis to yield the deprotected indazole 108-2 and further deprotected with TFA to render the desired product D-108.
Scheme V
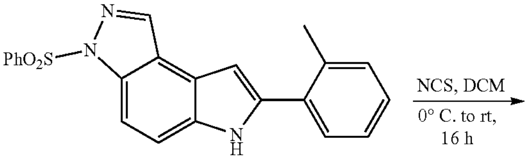
85-6
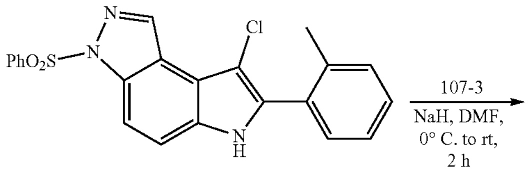
109-1
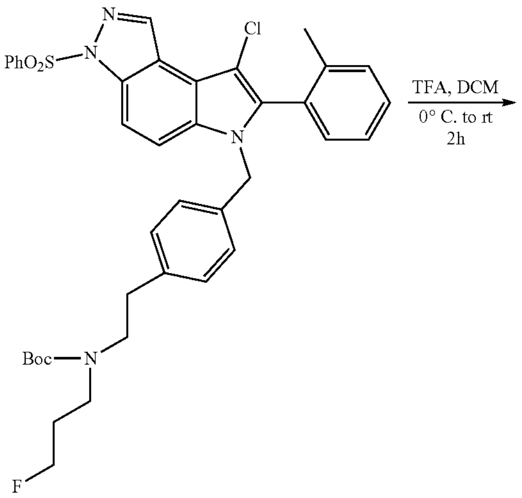
109-2
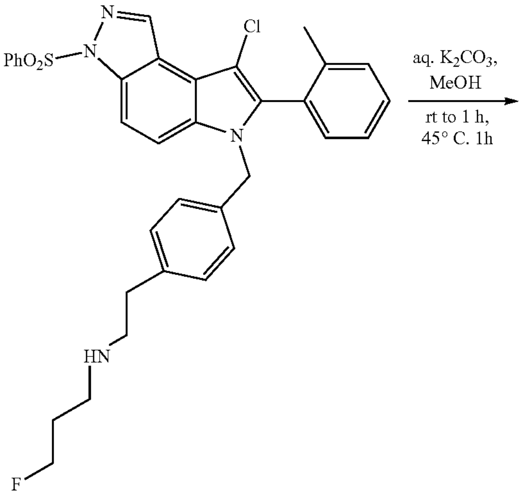
109-3

-continued
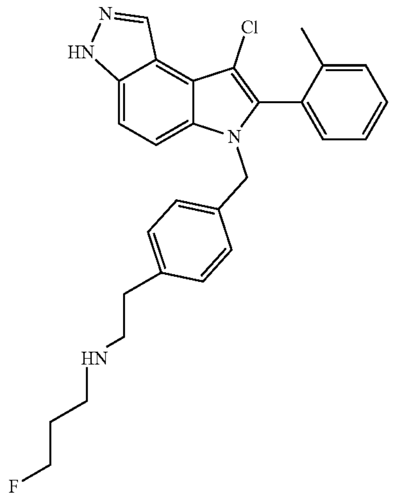
D-109
Referring now to Scheme V, scaffold 85-6 was chlorinated at the 3-position with NCS to yield the 3-Cl indole scaffold 109-1 which was subsequently alkylated with the sidechain 107-3 which was subsequently deprotected with TFA to render intermediate 109-3 followed by base to yield D-109.
Scheme VI
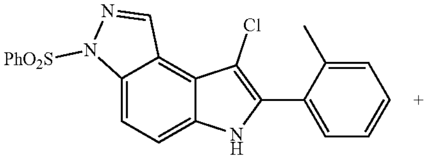
109-1
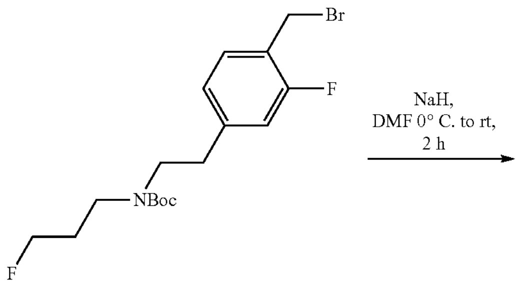
105-5
-continued
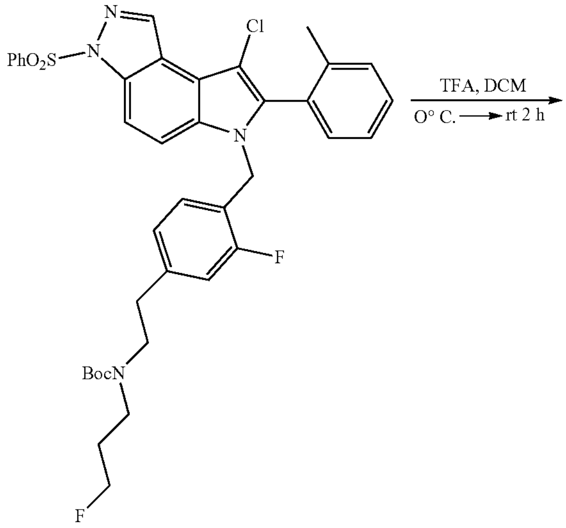
110-1
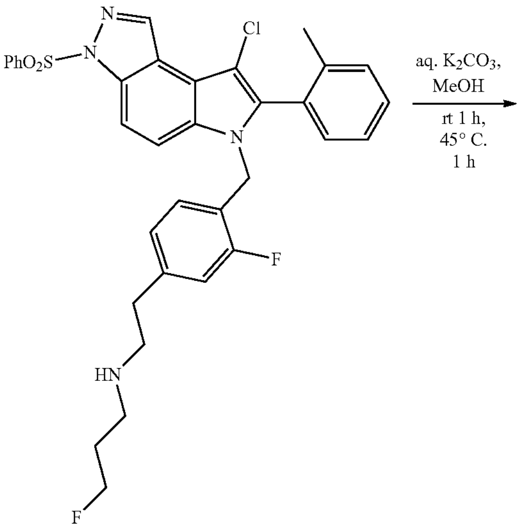
110-2
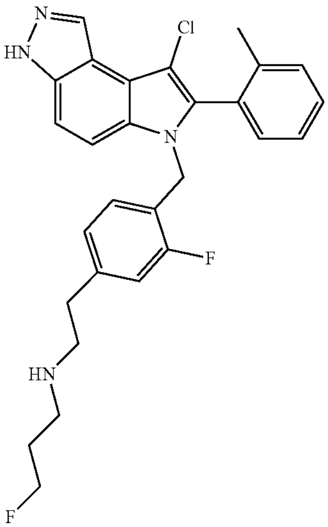
D-110

Scaffold 109-1 can be alkylated with 105-5 giving 110-1 as provided in Scheme VI that can be subsequently deprotected with TFA (removing the N-Boc group) and aqueous basic methanol (removing the phenylsulfonyl group) which can yield D-110.
Scheme VII
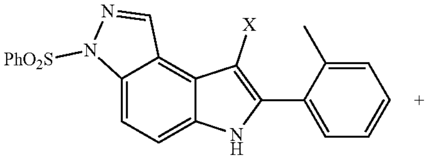
109-1 (X = Cl)
85-7 (X = F)
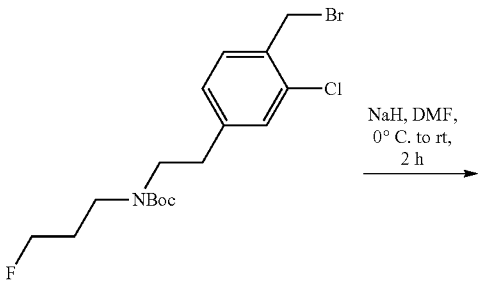
115-5
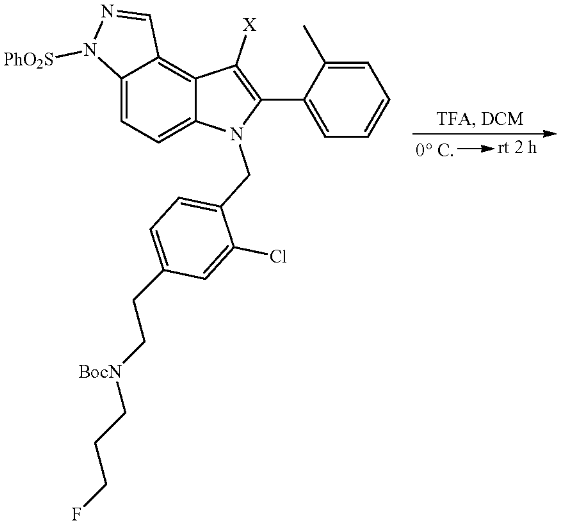
111-1 (X = Cl)
112-1 (X = F)
-continued
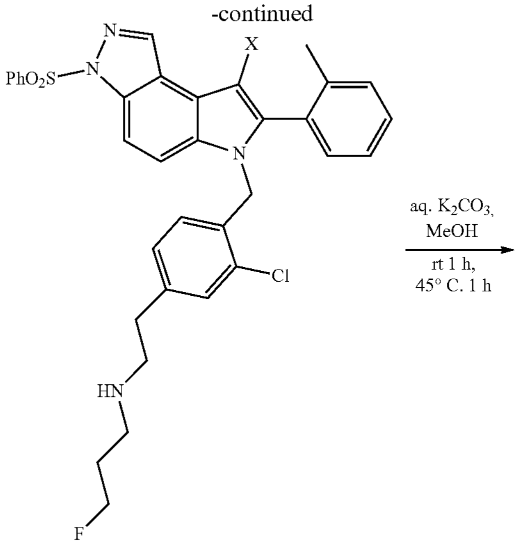
111-2 (X = Cl)
112-2 (X = F)
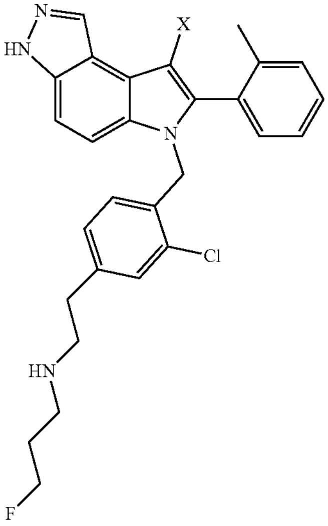
D-111 (X = Cl)
D-112 (X = F)
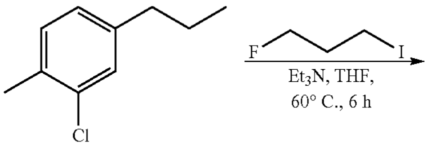
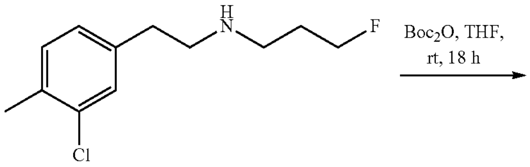
111-3
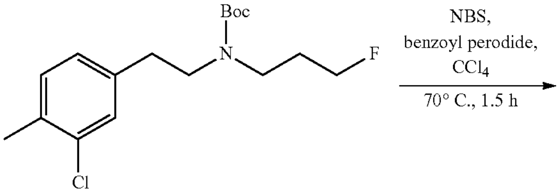
111-4

-continued

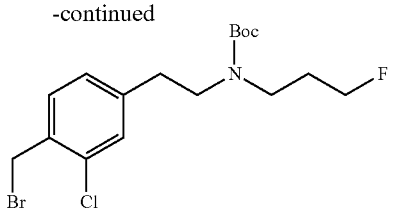

111-5

Referring now to Scheme VII, scaffolds 109-1 and 85-7 can be alkylated with 115-5 which can give 111-1 and 112-1 (respectively) which can subsequently be deprotected with TFA (removing the N-Boc group(s)) and aqueous basic methanol (removing the phenylsulfonyl group(s)) which can yield D-111/D112. The sidechain 115-5 can be prepared as shown in the lower part of the scheme.

EXAMPLES

Materials: all chemicals were reagent grade and used without further purification. Chromatographic elution solvent systems are reported as volume:volume ratios. LC-MS data were obtained using a LC Thermo Finnigan Surveyor-MS Thermo Finnigan AQA in either positive mode or negative mode as described below:

LCMS-Condition 01: Method:—LCMS_X-Select (Formic Acid)

Column: X-Select CSH C18 (4.6*50) mm 2.5 u, Mobile Phase: A.0.1% Formic acid in water B. 0.1% Formic acid in Acetonitrile, Inj Volume: 5.0 μL, Flow Rate: 1.0. mL/minute, Gradient program: 2% B to 98% B in 2.8 minute, Hold till 4.8 min, At 5.0 min B conc is 2% up to 7.0 min.

LCMS-Condition 02: Method:—LCMS_X-Bridge ($NH_3$)

Column: X-Bridge C18 (3.0*50) mm 2.5μ; Mobile Phase: A. 0.05% $NH_3$ in water; B. 0.05% $NH_3$ in Acetonitrile, Inj Volume: 0.2 μL, Flow Rate: 1.0 mL/minute; Gradient program: 1% B to 90% B in 1.5 minute, 100% B in 2.5 minute, Hold till 2.8 minute, At 3.0 minute B conc is 1% up to 4.0 min.

LCMS-Condition 03: Method:—LCMS_X-Select (Ammonium Bicarbonate)

Column: X-Select CSH C18 (3.0*50) mm 2.5 u; Mobile Phase: A: 5 mM Ammonium Bicarbonate) in water; B: Acetonitrile; Inj Volume: 2 μL, Flow Rate: 1.2 mL/minute; Column oven temp. 50 C; Gradient program: 0% B to 98% B in 2.0 minute, hold till 3.0 min, at 3.2 min B conc is 0% up to 4.0 min.

Example 1: Synthesis of 3-fluoro-N-(3-fluoro-4-((8-fluoro-7-(o-tolyl)pyrrolo[3,2-e]indazol-6(3H)-yl)methyl)phenethyl)propan-1-amine (D-105)

Step 1

To 2-(3-fluoro-4-methylphenyl)acetonitrile 105-1 (5.00 g, 33.55 mmol) in THE (60 mL) at 0° C. was added $BH_3$·DMS (7.65 g, 100.67 mmol) under argon atmosphere. The reaction mixture was further heated to 70° C. for 5 h. After completion of the reaction (monitored by TLC), the reaction mixture was cooled to 0° C., quenched with mixture of 1N HCl (10 mL) and methanol (10 mL) dropwise and heated to 70° C. for 1 h. The reaction mixture was concentrated under reduced pressure resulting in the crude compound. The crude compound was purified by trituration with diethyl ether, filtered and dried to afford 5.00 g (78.7% yield) of 105-2 (HCl) as a white solid.

LCMS-Condition-1: $[M+H]^+$=154.50; Rt=0.792 min $^1$H NMR (400 MHz, DMSO-$d_6$) δ: 8.15 (br. s, 3H), 7.23 (t, J=7.82 Hz, 1H), 7.07 (d, J=10.27 Hz, 1H), 6.99 (d, J=7.34 Hz, 1H), 6.53 (br. s, 1H), 3.00 (br. s, 2H), 2.84-2.90 (m, 2H), 2.20 (s, 3H).

Step 2

To 2-(3-fluoro-4-methylphenyl)ethan-1-amine hydrochloride salt 105-2 (5.00 g, 26.36 mmol) in THE (80 mL) was added triethyl amine (15.3 mL, 110.62 mmol) stirred for 10 min, followed by addition of 1-fluoro-3-iodopropane 3 (7.48 g, 39.82 mmol) at room temperature under argon atmosphere. The reaction mixture was further heated to 70° C. and stirred for 6 h. After consumption of 105-2 and 1-Iodo-3-fluoropropane (monitored by TLC), showed formation of 3-fluoro-N-(3-fluoro-4-methylphenethyl)propan-1-amine 105-3. To the resulting solution was added Boc anhydride (14.5 g, 66.37 mmol) at room temperature and stirred for 18 h. After completion of the reaction (monitored by TLC), the reaction mixture was diluted with water (100 mL) and extracted with ethyl acetate (2×100 mL). The combined organic layer was washed with water (2×40 mL), brine (40 mL), dried over anhydrous $Na_2SO_4$, filtered and concentrated under reduced pressure. The resulting crude compound was purified by silica gel column chromatography eluting with 0-30% ethyl acetate in n-hexane to afford 2.14 g (31% yield) of 105-4 as colorless oil.

LCMS-Condition-1: $[M-tBu]^+$=258.30; Rt=2.216 min $^1$H NMR (400 MHz, $CDCl_3$) δ: 7.08 (t, J=7.83 Hz, 1H), 6.79-6.88 (m, 2H), 4.35-4.54 (m, 2H), 3.35-3.41 (m, 2H), 3.19-3.31 (m, 2H), 2.73-2.84 (m, 2H), 2.23 (s, 3H), 1.79-1.99 (m, 2H), 1.44 (br. s, 9H).

Step 3

To tert-butyl (3-fluoro-4-methylphenethyl)(3-fluoropropyl)carbamate 105-4 (2.10 g, 6.709 mmol) in $CCl_4$ (30 mL) was added NBS (1.55 g, 8.722 mmol) and benzoyl peroxide (0.081 g, 0.335 mmol) at room temperature under argon atmosphere. The reaction mixture was further heated at 70° C. for 1.5 h. After completion of the reaction (monitored by TLC), the reaction mixture was cooled to 0° C. and diluted with water. The separated aqueous layer was extracted with $CH_2Cl_2$ (2×50 mL). The combined organic layer was washed with water (40 mL) and brine (30 mL), dried over anhydrous $Na_2SO_4$, filtered and concentrated under reduced pressure resulting in the crude compound as brown solid. The crude compound was purified by silica gel column chromatography eluting with 0-15% ethyl acetate in n-hexane to afford 0.675 g (26% yield) of 105-5 as colorless thick oil.

LCMS-Condition-1: $[M-18]^+$=375.00; Rt=2.241 min $^1$H NMR (400 MHz, $CDCl_3$) δ: 8.11 (d, J=7.34 Hz, 1H), 7.48 (t, J=7.83 Hz, 1H), 7.27-7.34 (m, 1H), 4.50 (s, 2H), 3.36-3.44 (m, 2H), 3.26 (d, J=14.18 Hz, 2H), 2.74-2.88 (m, 2H), 2.19-2.31 (m, 1H), 1.79-1.99 (m, 3H), 1.44 (br. s, 9H).

Step 4

To 8-fluoro-3-(phenylsulfonyl)-7-(o-tolyl)-3,6-dihydropyrrolo[3,2-e]indazole 85-7 (1.02 g, 2.518 mmol) in DMF (10 mL) at 0° C. was added sodium hydride (60% dispersion in oil, 0.252 g, 6.295 mmol) portionwise. The reaction mixture was allowed to attain room temperature for 10 min. The resulting solution was cooled to 0° C. and tert-butyl (4-(bromomethyl)-3-fluorophenethyl)(3-fluoropropyl)carbamate (1.18 g, 3.010 mmol) was added to it. The reaction mixture was allowed to attain room temperature and stirred for 2 h. After completion of the reaction (monitored by TLC), the reaction mixture was cooled to 0° C. and diluted with water (100 mL). The aqueous layer was separated and extracted with ethyl acetate (2×100 mL). The combined organic layer was washed with water (2×40 mL) and brine (40 mL), dried over anhydrous $Na_2SO_4$, filtered and concentrated under reduced pressure resulting in the crude compound as a brown solid. The resulting crude compound was purified by silica gel column chromatography eluting with 0-2% methanol in DCM to afford the title compound 105-6 0.121 g (12% yield) and 105-7 0.520 g (37% yield) as light yellow solid.

105-6

LCMS-Condition-1: $[M+Na]^+$=739.75; Rt=2.503 min 105-7

LCMS-Condition-1: $[M-tBu]^+$=521.60; Rt=2.301 min $^1H$ NMR (400 MHz, DMSO-$d_6$) δ: 13.22 (br. s, 1H), 8.17 (s, 1H), 7.52 (br. s, 1H), 7.26-7.42 (m, 5H), 6.93 (d, J=10.76 Hz, 1H), 6.78 (d, J=7.34 Hz, 1H), 6.30 (t, J=7.83 Hz, 1H), 5.22-5.41 (m, 2H), 4.43 (d, J=5.38 Hz, 1H), 4.31 (t, J=4.89 Hz, 1H), 3.23-3.29 (m, 2H), 3.13 (br. s, 2H), 2.63-2.69 (m, 2H), 2.11 (br. s, 3H), 1.69-1.81 (m, 2H), 1.32 (br. s, 4H), 1.24 (br. s, 5H).

Step 5

To tert-butyl (3-fluoro-4-((8-fluoro-7-(o-tolyl)pyrrolo[3,2-e]indazol-6(3H)-yl)methyl)phenethyl)(3-fluoropropyl) carbamate 105-7 (0.250 g, 0.434 mmol) in diethyl ether (5 mL) at 0° C. was added 4M dioxane in HCl solution (2 mL). The reaction mixture was allowed to attain room temperature and stirred for 18 h. After completion of the reaction (monitored by TLC), the reaction mixture was concentrated under reduced pressure resulting in the crude compound as HCl salt which was washed with n-hexane, filtered and dried. The crude compound was purified by preparative HPLC to afford 0.080 g (39% yield) of D-108 as an off white solid.

LCMS-Condition-1: $[M+H]^+$=477.55; Rt=1.456 min $^1H$ NMR (400 MHz, DMSO-$d_6$) δ: 13.22 (br. s, 1H), 8.17 (br. s, 1H), 7.56 (d, J=9.29 Hz, 1H), 7.26-7.44 (m, 5H), 6.94 (d, J=11.25 Hz, 1H), 6.79 (d, J=7.83 Hz, 1H), 6.29 (t, J=7.82 Hz, 1H), 5.20-5.41 (m, 2H), 4.50 (t, J=5.62 Hz, 1H), 4.38 (t, J=5.62 Hz, 1H), 2.53-2.66 (m, 7H), 2.09 (s, 3H), 1.66-1.75 (m, 2H).

Example 2: Synthesis of N-(3,5-difluoro-4-((8-fluoro-7-(o-tolyl)pyrrolo[3,2-e]indazol-6(3H)-yl)methyl)phenethyl)-3-fluoropropan-1-amine (D-106)

Step 1

To 4-bromo-2,6-difluorobenzaldehyde (15.0 g, 67.84 mmol) in DMA (220 mL) was added methyl acrylate (9.20 mL, 8.74 g, 101.52 mmol), triphenyl phosphine (1.77 g, 6.756 mmol) and triethyl amine (18.8 mL, 135.14 mmol) at room temperature and degassed with nitrogen for 10 min. To the resulting solution was added $Pd(OAc)_2$ (0.759 g, 3.388 mmol) and degassed with nitrogen for another 10 min at room temperature. The reaction mixture was further heated to 80° C. and stirred for 6 h. After completion of the reaction (monitored by TLC), the reaction mixture was diluted with water (100 mL) and extracted with ethyl acetate (2×100 mL). The combined organic layer was dried over anhydrous $Na_2SO_4$, filtered and concentrated under reduced pressure. The resulting crude compound was purified by silica gel column chromatography eluting with 0-4% ethyl acetate in n-hexane to afford 15.0 g (98.0% yield) of 106-1 as a yellow solid.

$^1H$ NMR (400 MHz, DMSO-$d_6$) δ: 10.19 (s, 1H), 7.73 (d, J=10.27 Hz, 2H), 7.67 (d, J=16.14 Hz, 1H), 6.95 (d, J=16.14 Hz, 1H), 3.75 (s, 3H).

Step 2

To methyl (E)-3-(3,5-difluoro-4-formylphenyl)acrylate 106-1 (6.00 g, 26.43 mmol) in methanol (120 mL) and ethyl acetate (2 mL) was added 10% $PtO_2$ (0.600 g, 2.643 mmol) at room temperature under nitrogen atmosphere. The reaction mixture was further stirred under hydrogen atmosphere using hydrogen bladder at room temperature for 16 h. After completion of the reaction (monitored by TLC), the reaction mixture was filtered through a pad of Celite and washed with methanol (200 mL). The filtrate was concentrated under reduced pressure resulting in the crude compound. The crude compound was purified by silica gel column chromatography eluting with 0-30% ethyl acetate in n-hexane to afford 6.00 g (99.6% yield) of 106-2 as a colorless oil.

LCMS-Condition-1: $[M+ACN]^+$=269.90; Rt=1.995 min $^1H$ NMR (400 MHz, DMSO-$d_6$) δ: 10.16 (s, 1H), 7.18 (d, J=10.27 Hz, 2H), 3.59 (s, 3H), 2.90-2.96 (m, 2H), 2.69-2.75 (m, 2H).

Step 3

To methyl 3-(3,5-difluoro-4-formylphenyl)propanoate 106-2 (6.00 g, 26.29 mmol) in methanol (70 mL) at 0° C. was added sodium borohydride (0.500 g, 13.20 mmol). The reaction mixture was allowed to attain room temperature and stirred for 1 h. After completion of the reaction (monitored by TLC), the reaction mixture was diluted with water (50 mL) and extracted with DCM (3×50 mL). The combined organic layer was dried over anhydrous $Na_2SO_4$, filtered and concentrated under reduced pressure to afford 2.80 g (46.3% yield) of 106-3 as a colorless oil.

LCMS-Condition-1: $[M-H_2O]^+$=212.70; Rt=1.768 min $^1H$ NMR (400 MHz, DMSO-$d_6$) δ: 6.83-6.87 (m, 2H), 5.06 (t, J=5.62 Hz, 1H), 4.33 (d, J=5.87 Hz, 2H), 3.47 (s, 3H), 2.69-2.77 (m, 2H), 2.50-2.59 (m, 2H).

Step 4

To a solution of methyl 3-(3,5-difluoro-4-(hydroxymethyl)phenyl)propanoate 106-3 (4.50 g, 19.54 mmol) in DMF (50 mL) at 0° C. was added sodium hydride (60% dispersion in oil, 1.17 g, 29.32 mmol) portionwise and stirred for 20 min. To the resulting solution at 0° C. was added benzyl bromide (3.48 mL, 29.32 mmol) to it. The reaction mixture was allowed to attain room temperature and stirred for 4 h. After completion of the reaction (monitored by TLC), the reaction mixture was diluted with water (100 mL) and extracted with ethyl acetate (2×50 mL). The combined organic layer was dried over anhydrous $Na_2SO_4$, filtered and concentrated under reduced pressure resulting in the crude compound as a brown solid. The resulting crude compound was purified by 100-200 mesh size silica gel column chromatography eluting with 0-3% ethyl acetate in n-hexane to afford 6.00 g (95.8% yield) of 106-4 as a colorless oil.

LCMS-Condition-1: $[M+Na]^+$=343.90; Rt=2.326 min $^1H$ NMR (400 MHz, DMSO-$d_6$) δ: 7.27-7.38 (m, 5H), 7.03 (d, J=8.31 Hz, 2H), 4.51 (s, 4H), 3.58 (s, 3H), 2.86 (d, J=7.83 Hz, 2H), 2.63-2.70 (m, 2H).

Step 5

To methyl 3-(4-((benzyloxy)methyl)-3,5-difluorophenyl) propanoate 106-4 (5.50 g, 17.16 mmol) in THE or methanol (40 mL) was added solution of lithium hydroxide (7.48 g, 39.82 mmol) in water (20 mL) at room temperature and stirred for 1 h. After completion of the reaction (monitored by TLC), the reaction mixture was concentrated under reduced pressure, diluted with water (50 mL) and extracted with ethyl acetate (3×50 mL). The aqueous layer was acidify using citric acid upto pH=2 and extracted with ethyl acetate (3×50 mL). The combined organic layer was dried over anhydrous $Na_2SO_4$, filtered and concentrated under reduced pressure to afford 5.00 g (95.2% yield) of the title compound 106-5 as colorless oil.

$^1H$ NMR (400 MHz, DMSO-$d_6$) δ: 12.13 (br. s, 1H), 7.25-7.38 (m, 5H), 7.02 (d, J=8.31 Hz, 2H), 4.51 (s, 4H), 2.79-2.87 (m, 2H), 2.57 (t, J=7.58 Hz, 2H).

Step 6

To 3-(4-((benzyloxy)methyl)-3,5-difluorophenyl)propanoic acid 106-5 (5.00 g, 16.32 mmol) in DCM (50 mL) was added thionyl chloride (11.8 mL, 163.23 mmol) at room temperature under nitrogen atmosphere. The reaction mixture was further heated to reflux at 75° C. for 4 h. After completion of the reaction (monitored by TLC), the reaction mixture was concentrated under reduced pressure upto dryness under nitrogen atmosphere. The resulting corresponding acid chloride of 106-5 (5.00 g, 15.39 mmol) was added dry acetone (50 mL) followed by sodium azide (2.00 g, 30.76 mmol) at room temperature under nitrogen atmosphere and stirred for 3 h. After completion of the reaction (monitored by TLC), the reaction mixture was concentrated under reduced pressure under nitrogen atmosphere upto dryness. To the resulting azide intermediate of 106-5 (4.50 g, 14.83 mmol) was added tert-butanol (40 mL) at room temperature under nitrogen atmosphere. The reaction mixture was further heated to reflux at 85° C. for 18 h. After completion of the reaction (monitored by TLC), the reaction mixture was concentrated under reduced pressure upto dryness resulting in the crude Boc-protected 106-6 compound. The crude compound was purified by silica gel column chromatography eluting with 0-10% ethyl acetate in n-hexane to yield 3 g of Boc-protected 106-6 as colorless oil. Boc-protected 106-6 was dissolved in DCM (25 mL) and trifluoroacetic acid (5 mL) added dropwise at room temperature and stirred for 3 h. After completion of the reaction (monitored by TLC), the reaction mixture was concentrated under reduced pressure upto dryness to afford 2.20 g (48.5% yield) of 106-6 as a colorless oil.

LCMS-Condition-1: $[M+H]^+$=277.90; Rt=1.467 min $^1H$ NMR (400 MHz, DMSO-$d_6$) δ: 7.25-7.38 (m, 5H), 6.98 (d, J=8.37 Hz, 2H), 4.51 (s, 4H), 2.76-2.83 (m, 2H), 2.64-2.70 (m, 2H).

Step 7

To 2-(4-((benzyloxy)methyl)-3,5-difluorophenyl)ethan-1-amine 106-6 (2.20 g, 7.933 mmol) in THE (20 mL) was added triethyl amine (3.29 mL, 23.72 mmol) followed by solution of 1-fluoro-3-iodopropane (1.49 g, 7.933 mmol) in THE (10 mL) at room temperature under argon atmosphere. The reaction mixture was further heated to 80° C. and stirred for 18 h in a seal tube. After completion of the reaction (monitored by TLC), the reaction mixture was concentrated under reduced pressure resulting in the crude compound. The crude compound was purified by 100-200 mesh size silica gel column chromatography eluting with 0-5% methanol in DCM to afford 1.60 g (59.9% yield) of 106-7 as a thick brown thick oil.

LCMS-Condition-1: $[M+H]^+$=338.10; Rt=1.612 min $^1H$ NMR (400 MHz, DMSO-$d_6$) δ: 7.25-7.39 (m, 5H), 7.01 (d, J=7.88 Hz, 2H), 4.53-4.55 (m, 1H), 4.51 (s, 4H), 4.37-4.46 (m, 1H), 2.75 (dd, J=4.92, 10.83 Hz, 4H), 2.63 (t, J=6.64 Hz, 2H), 1.66-1.87 (m, 2H).

Step 8

To a stirred solution of N-(4-((benzyloxy)methyl)-3,5-difluorophenethyl)-3-fluoropropan-1-amine 106-7 (1.60 g, 4.742 mmol) in DCM (30 mL) at 0° C. was added triethyl amine (1.96 mL, 14.13 mmol) and stirred for 10 min. To the resulting solution was added Boc anhydride (1.55 g, 7.110 mmol) at the same temperature. The reaction mixture was allowed to attain room temperature under and stirred for 3 h. After completion of the reaction (monitored by TLC), the reaction mixture was diluted with water (100 mL) and extracted with DCM (2×100 mL). The combined organic layer was dried over anhydrous $Na_2SO_4$, filtered and concentrated under reduced pressure. The resulting crude compound was purified by 100-200 mesh size silica gel column chromatography eluting with 0-20% ethyl acetate in n-hexane to afford 1.80 g (86.9% yield) of the 106-8 as a yellow oil.

LCMS-Condition-1: $[M-Boc]^+$=337.90; Rt=2.490 min $^1H$ NMR (400 MHz, DMSO-$d_6$) δ: 7.24-7.38 (m, 5H), 6.98 (d, J=7.88 Hz, 2H), 4.46-4.56 (m, 4H), 4.36 (t, J=5.91 Hz, 1H), 3.38 (t, J=6.89 Hz, 2H), 3.22 (br. s, 2H), 2.79 (t, J=6.89 Hz, 2H), 1.75-1.90 (m, 2H), 1.35 (br. s, 4H), 1.30 (br. s, 5H), 1.17 (t, J=7.14 Hz, 1H).

Step 9

To tert-butyl (4-((benzyloxy)methyl)-3,5-difluorophenethyl)(3-fluoropropyl)carbamate 106-8 (1.80 g, 4.114 mmol) in methanol:ethyl acetate (1:1; 100 mL) was added 10% Pd/C (50% moisture; 0.800 g) at room temperature under nitrogen atmosphere. The reaction mixture was further stirred under hydrogen atmosphere at room temperature for 8 h. After completion of the reaction (monitored by TLC), the reaction mixture was filtered through a pad of Celite and washed with methanol (200 mL). The filtrate was concentrated under reduced pressure to afford 1.40 g (98.6% yield) of 106-9 as a colorless sticky liquid.

LCMS-Condition-1: $[M-Boc]^+$=248.00; Rt=2.168 min $^1H$ NMR (400 MHz, DMSO-$d_6$) δ: 6.92 (d, J=7.88 Hz, 2H), 5.17 (br. s, 1H), 4.43-4.51 (m, 3H), 4.36 (t, J=5.91 Hz, 1H), 3.36 (t, J=7.14 Hz, 2H), 3.22 (t, J=6.64 Hz, 2H), 2.77 (t, J=7.14 Hz, 2H), 1.74-1.90 (m, 2H), 1.33 (br. s, 9H).

Step 10

To tert-butyl (3,5-difluoro-4-(hydroxymethyl)phenethyl)(3-fluoropropyl)carbamate 106-9 (1.40 g, 4.030 mmol) in DCM (50 mL) at 0° C. was added triphenyl phosphine (1.58 g, 6.055 mmol) and carbon tetrabromide (2.00 g, 6.048 mmol) portionwise. The reaction mixture was allowed to attain room temperature and stirred for 5 h. After completion of the reaction (monitored by TLC), the reaction mixture was diluted with water (100 mL) and extracted with ethyl acetate (3×100 mL). The combined organic layer was dried over anhydrous $Na_2SO_4$, filtered and concentrated under reduced pressure. The resulting crude compound was purified by silica gel column chromatography eluting with 0-40% ethyl acetate in n-hexane to afford 1.20 g (72.7% yield) of 106-10 as an off white solid.

LCMS-Condition-1: $[M+ACN+Na]^+$=474.30; Rt=1.640 min $^1H$ NMR (400 MHz, DMSO-$d_6$) δ: 7.02 (d, J=8.37 Hz, 2H), 4.62 (s, 2H), 4.48 (t, J=5.91 Hz, 1H), 4.36 (t, J=5.66 Hz, 1H), 3.39 (t, J=6.64 Hz, 2H), 3.23 (br. s, 2H), 2.79 (t, J=6.89 Hz, 2H), 1.75-1.90 (m, 2H), 1.35 (br. s, 4H), 1.29 (br. s, 5H)

Step 11

To 8-fluoro-3-(phenylsulfonyl)-7-(o-tolyl)-3,6-dihydropyrrolo[3,2-e]indazole (0.700 g, 1.726 mmol) 85-7 in DMF (10 mL) at 0° C. was added sodium hydride (60% dispersion in oil, 0.138 g, 3.452 mmol) portionwise. The reaction mixture was allowed to attain room temperature and stirred for 15 min. The resulting solution was cooled to 0° C. and tert-butyl (4-(bromomethyl)-3,5-difluorophenethyl)(3-fluoropropyl)carbamate 106-10 (0.921 g, 2.245 mmol) was added to it. The reaction mixture was allowed to attain room temperature and stirred for 2 h. After completion of the reaction (monitored by TLC), the reaction mixture was cooled to 0° C. and diluted with water (100 mL). The aqueous layer was separated and extracted with ethyl acetate (2×50 mL). The combined organic layer was washed with water (40 mL) followed by brine (30 mL), dried over anhydrous $Na_2SO_4$, filtered and concentrated under reduced pressure resulting in the crude compound as a brown solid. The resulting crude compound was purified by 100-200 mesh size silica gel column chromatography eluting with 0-30% ethyl acetate in n-hexane to afford 1.20 g (95% yield) of 106-11 as a thick brown oil.

LCMS-Condition-1: $[M\text{-}tBu]^+$=679.20; Rt=1.850 min

Step 12

To tert-butyl (3,5-difluoro-4-((8-fluoro-3-(phenylsulfonyl)-7-(o-tolyl)pyrrolo[3,2-e]indazol-6(3H)-yl)methyl) phenethyl)(3-fluoropropyl)carbamate 106-11 (1.20 g, 1.633 mmol) in DCM (15 mL) at 0° C. was added trifluoroacetic acid (5 mL) dropwise. The reaction mixture was allowed to attain room temperature and stirred for 2 h. After completion of the reaction (monitored by TLC), the reaction mixture was concentrated under reduced pressure resulting in the crude residue. The crude residue was diluted with DCM (50 mL) and washed with saturated $NaHCO_3$ solution (2×25 mL). The organic layer was separated, dried over anhydrous $Na_2SO_4$, filtered and concentrated under reduced pressure resulting in the crude compound. The resulting crude compound was purified by 100-200 mesh size silica gel column chromatography eluting with 0-8% methanol in DCM to afford 0.700 g (67.9% yield) of 106-12 as a sticky brown oil.

LCMS-Condition-1: $[M-H_2O]^+$=617.20; Rt=1.715 min $^1$H NMR (400 MHz, DMSO-$d_6$) δ: 8.56 (s, 1H), 7.92 (s, 1H), 7.85 (d, J=6.85 Hz, 2H), 7.78-7.83 (m, 1H), 7.58-7.63 (m, 1H), 7.49 (t, J=7.83 Hz, 2H), 7.25-7.31 (m, 1H), 7.11-7.21 (m, 3H), 6.64 (d, J=8.80 Hz, 2H), 5.65 (d, J=0.98 Hz, 1H), 5.21-5.41 (m, 2H), 4.40 (t, J=5.62 Hz, 1H), 4.28 (t, J=5.62 Hz, 1H), 2.42-2.57 (m, 6H), 1.77 (s, 2H), 1.54-1.68 (m, 3H).

Step 13

To N-(3,5-difluoro-4-((8-fluoro-3-(phenylsulfonyl)-7-(o-tolyl)pyrrolo[3,2-e]indazol-6(3H)-yl)methyl)phenethyl)-3-fluoropropan-1-amine 106-12 (0.700 g, 1.102 mmol) in methanol (25 mL) was added aqueous solution of potassium carbonate (0.305 g, 2.208 mmol) at room temperature and stirred for 1 h. The reaction mixture was further heated at 45° C. for 1 h. After completion of the reaction (monitored by TLC), the reaction mixture was concentrated under reduced pressure, diluted with water (20 mL) and extracted with ethyl acetate (3×20 mL). The combined organic layer was dried over anhydrous $Na_2SO_4$, filtered and concentrated under reduced pressure resulting in the crude compound. The crude compound was purified by Combi Flash column chromatography eluting with 0-10% methanol in DCM to afford 0.010 g (11.0% yield) of D-106 as an off white solid.

LCMS-Condition-1: $[M+H]^+$=495.15; Rt=1.492 min $^1$H NMR (400 MHz, DMSO-$d_6$) δ: 13.18 (br. s, 1H), 8.12 (br. s, 1H), 7.63 (d, J=9.29 Hz, 1H), 7.26-7.41 (m, 5H), 6.75 (d, J=9.29 Hz, 2H), 5.30-5.42 (m, 2H), 4.50 (t, J=5.87 Hz, 1H), 4.38 (t, J=6.11 Hz, 1H), 2.53-2.66 (m, 6H), 1.97 (s, 3H), 1.63-1.78 (m, 3H).

Example 3: Synthesis of N-(4-((1,8-difluoro-7-(o-tolyl)pyrrolo[3,2-e]indazol-6(3H)-yl)methyl)phenethyl)-3-fluoropropan-1-amine (D-107)

Step 1

To 2-(p-tolyl)ethan-1-amine (20.0 g, 147.91 mmol) in THF (300 mL) was added triethyl amine (61.6 mL, 444.35 mmol) and 1-fluoro-3-iodopropane 2 (27.8 g, 147.91 mmol) at room temperature under argon atmosphere. The reaction mixture was further heated to 80° C. and stirred for 18 h. After completion of the reaction (monitored by TLC), the reaction mixture was concentrated under reduced pressure resulting in the crude compound. The crude compound was purified by 100-200 mesh size silica gel column chromatography eluting with 0-2% methanol in DCM to afford 12.0 g (45.4% yield) 107-1 as a colorless thick oil.

LCMS-Condition-1: $[M+H]^+$=195.90; Rt=1.042 min $^1$H NMR (400 MHz, DMSO-$d_6$) δ: 7.04-7.13 (m, 4H), 4.54 (t, J=5.87 Hz, 1H), 4.42 (t, J=5.87 Hz, 1H), 3.07 (br. s, 1H), 2.70-2.75 (m, 2H), 2.61-2.68 (m, 4H), 2.25 (s, 3H), 1.70-1.84 (m, 2H).

Step 2

To 3-fluoro-N-(4-methylphenethyl)propan-1-amine 107-1 (12.0 g, 61.45 mmol) in DCM or THF (250 mL) at 0° C. was added triethyl amine (25.6 mL, 184.35 mmol) followed by Boc anhydride (20.1 g, 92.20 mmol) and stirred at the same temperature for 10 min. The reaction mixture was allowed to attain room temperature and stirred for 6 h. After completion of the reaction (monitored by TLC), the reaction mixture was diluted with water (100 mL) and extracted with DCM (3×100 mL). The combined organic layer was dried over anhydrous $Na_2SO_4$, filtered and concentrated under reduced pressure. The resulting crude compound was purified by silica gel column chromatography eluting with 0-10% ethyl acetate in n-hexane to afford 12.0 g (66.2% yield) of 107-2 as a yellow oil.

LCMS-Condition-1: $[M+Na]^+$=318.15; Rt=2.294 min $^1$H NMR (400 MHz, DMSO-$d_6$) δ: 7.04-7.13 (m, 4H), 4.47 (t, J=5.87 Hz, 1H), 4.35 (t, J=5.87 Hz, 1H), 3.29 (d, J=7.83 Hz, 2H), 3.19 (t, J=6.36 Hz, 2H), 2.71 (t, J=7.58 Hz, 2H), 2.26 (s, 3H), 1.72-1.89 (m, 2H), 1.35 (br. s, 9H).

Step 3

To tert-butyl (3-fluoropropyl)(4-methylphenethyl)carbamate 107-2 (17.0 g, 57.54 mmol) in $CCl_4$ (170 mL) was added NBS (15.4 g, 86.41 mmol) and benzoyl peroxide (1.39 g, 5.738 mmol) at room temperature under argon atmosphere. The reaction mixture was further heated at 70° C. for 2 h. After completion of the reaction (monitored by TLC), the reaction mixture was filtered through a pad of Celite and the filtrate obtained was concentrated under reduced pressure resulting in the crude compound. The crude compound was purified by 100-200 mesh size silica gel column chromatography eluting with 0-20% ethyl acetate in n-hexane to afford 7.00 g (32.5% yield) of 107-3 as a yellow oil.

LCMS-Condition-1: $[M+Na]^+$=398.05; Rt=2.262 min $^1$H NMR (400 MHz, DMSO-$d_6$) δ: 7.37 (d, J=7.83 Hz, 2H), 7.19 (d, J=6.85 Hz, 2H), 4.68 (s, 2H), 4.47 (t, J=5.87 Hz, 1H), 4.35 (t, J=5.87 Hz, 1H), 3.17-3.24 (m, 3H), 2.76 (t, J=7.34 Hz, 2H), 1.74-1.88 (m, 3H), 1.33 (br. s, 9H).

Step 4

To 5-nitro-1H-indazole (10.0 g, 61.34 mmol) in acetonitrile:acetic acid (1:1; 100 mL) was added Selectfluor (43.4 g, 122.67 mmol) at room temperature. The reaction mixture was further heated at 130° C. for 24 h. After completion of the reaction, the reaction mixture was quenched with ice cold water and the solid precipitated was filtered and dried resulting in the crude compound. The crude compound was purified by 100-200 mesh size silica gel column chromatography eluting with 0-10% ethyl acetate in n-hexane to afford 5.00 g (45% yield) of 107-4 as a pale yellow solid.

$^1$H NMR (400 MHz, DMSO-$d_6$) δ: 13.30 (br. s, 1H), 8.76 (d, J=1.96 Hz, 1H), 8.25 (dd, J=1.96, 9.29 Hz, 1H), 7.70 (dd, J=1.96, 9.29 Hz, 1H)

Step 5

To 3-fluoro-5-nitro-1H-indazole 107-4 (10 g, 55.25 mmol) in THE (100 mL) was added sodium hydroxide (5.52 g, 138.12 mmol), n-tetrabutyl ammonium sulfate (0.281 g, 0.827 mmol) at room temperature and stirred for 1 h. To the resulting solution was added benzene sulfonyl chloride (10.7 g, 60.58 mmol) dropwise and stirred for another 1 h. After completion of the reaction (monitored by TLC), the reaction mixture was quenched with water (100 mL) and the solid precipitated was filtered and dried to afford 14.0 g (78.8% yield) of 107-5 as a white solid.

LCMS-Condition-1: $[M-18]^+$=304.00; Rt=1.992 min $^1$H NMR (400 MHz, $CDCl_3$) δ: 8.59-8.63 (m, 1H), 8.51 (dd, J=1.97, 9.35 Hz, 1H), 8.35 (d, J=8.37 Hz, 1H), 8.02 (d, J=8.37 Hz, 2H), 7.62-7.70 (m, 1H), 7.54 (t, J=7.88 Hz, 2H).

Step 6

To 3-fluoro-5-nitro-1-(phenylsulfonyl)-1H-indazole 107-5 (14.0 g, 43.57 mmol) in methanol (140 mL) and water (60 mL) was added iron powder (0.407 g, 7.288 mmol) and ammonium chloride (23.27 g, 435.03 mmol) at room temperature. The reaction mixture was further heated at 80° C. for 16 h. After completion of the reaction (monitored by TLC), the reaction mixture was filtered through a pad of Celite and washed with methanol (25 mL) and THF (25 mL). The filtrate was concentrated under reduced pressure upto dryness to afford 12.0 g (crude) of 107-6 as a brown solid which was used as such in the next step without further purification.

LCMS-Condition-1: $[M+Na]^+$=314.90; Rt=1.735 min

Step 7

To 3-fluoro-1-(phenylsulfonyl)-1H-indazol-5-amine 107-6 (12.0 g, 41.19 mmol) in acetonitrile (150 mL) was added NIS (12.06 g, 53.60 mmol) portionwise at room temperature and stirred for 2 h. After completion of the reaction, the reaction mixture was diluted with water (50 mL) and extracted with ethyl acetate (3×50 mL). The combined organic layer dried over anhydrous $Na_2SO_4$, filtered and concentrated under reduced pressure. The resulting crude compound was purified by 100-200 mesh size silica gel column chromatography eluting with 10-15% ethyl acetate in n-hexane to afford 6.00 g (34.8% yield) of 107-7 as a yellow solid.

LCMS-Condition-1: $[M+H]^+$=417.95; Rt=2.090 min $^1$H NMR (400 MHz, DMSO-$d_6$) δ: 7.88 (d, J=8.80 Hz, 1H), 7.83 (d, J=8.31 Hz, 2H), 7.69-7.75 (m, 1H), 7.56-7.63 (m, 2H), 7.17 (d, J=9.29 Hz, 1H), 5.66 (br. s, 2H).

Step 8

To 3-fluoro-4-iodo-1-(phenylsulfonyl)-1H-indazol-5-amine 107-7 (8.00 g, 19.17 mmol) in $CH_2Cl_2$ (100 mL) at 0° C. was added triethyl amine (10.6 mL, 76.70 mmol) and TFAA (5.40 mL, 8.05 g, 38.35 mmol). The reaction mixture was allowed to attain room temperature and stirred for 2 h. After completion of the reaction (monitored by TLC), the reaction mixture was diluted with water (50 mL) and extracted with $CH_2Cl_2$ (3×50 mL). The combined organic layer dried over anhydrous $Na_2SO_4$, filtered and concentrated under reduced pressure. The resulting crude compound was purified by 100-200 mesh size silica gel column chromatography eluting with 10-20% ethyl acetate in n-hexane to afford 9.50 g (96.5% yield) of 107-8 as a yellow solid.

$^1$H NMR (400 MHz, DMSO-$d_6$) δ: 8.08 (d, J=8.86 Hz, 1H), 7.92 (d, J=7.88 Hz, 2H), 7.72-7.79 (m, 2H), 7.58-7.65 (m, 2H).

Step 9

To a solution of 2,2,2-trifluoro-N-(3-fluoro-4-iodo-1-(phenylsulfonyl)-1H-indazol-5-yl)acetamide 107-8 (9.50 g, 18.51 mmol) in DMF (150 mL) was added copper iodide (0.353 g, 1.853 mmol), triethyl amine (12.8 mL, 92.31 mmol) at room temperature and degassed with argon for 30 min. To the resulting solution was added catalyst dichlorobis (triphenylphosphine)palladium(II) (1.29 g, 1.837 mmol) and 1-ethynyl-2-methylbenzene (2.58 g, 22.20 mmol) and degassed for another 30 min. The reaction mixture was further heated to 130° C. and stirred for 18 h. After completion of the reaction, the reaction mixture was filtered through a pad of Celite and the filtrate was diluted with water (50 mL) and extracted with ethyl acetate (3×50 mL). The combined organic layer dried over anhydrous $Na_2SO_4$, filtered and concentrated under reduced pressure. The resulting crude compound was purified by 100-200 mesh size silica gel column chromatography eluting with 10-20% ethyl acetate in n-hexane to afford 4.00 g (53.3% yield) of 107-9 as a yellow solid.

LCMS-Condition-1: $[M+H]^+$=405.90; Rt=2.151 and 2.275 min $^1$H NMR (400 MHz, DMSO-$d_6$) δ: 12.12 (br. s, 1H), 7.83-7.95 (m, 3H), 7.63-7.75 (m, 2H), 7.53-7.61 (m, 3H), 7.33 (d, J=3.91 Hz, 3H), 6.81 (s, 1H), 2.47 (br. s, 1H), 2.45 (s, 2H).

Step 10

To 1-fluoro-3-(phenylsulfonyl)-7-(o-tolyl)-3,6-dihydro-pyrrolo[3,2-e]indazole 107-9 (1 g, 2.466 mmol) in acetonitrile: DMSO (1:1; 20 mL) at −10° C. was added Selectfluor (3.14 g, 8.863 mmol) portionwise over a period of 1 h under nitrogen atmosphere. The reaction mixture was allowed to attain room temperature and stirred for 6 h. After completion of the reaction, the reaction mixture was concentrated under reduced pressure upto dryness and diluted with ethyl acetate (100 mL). The organic layer was separated, washed with water (30 mL) and brine (30 mL), dried over anhydrous $Na_2SO_4$, filtered and concentrated under reduced pressure. The resulting crude compound was purified by 100-200 mesh size silica gel column chromatography eluting with 0-10% ethyl acetate in n-hexane to afford 0.450 g (43% yield) of 107-10 as a brown solid.

LCMS-Condition-1: $[M+Na]^+$=445.95; Rt=2.296 min $^1$H NMR (400 MHz, $CDCl_3$) δ: 12.04 (br. s, 1H), 7.94-7.99 (m, 1H), 7.90 (d, J=7.98 Hz, 2H), 7.78-7.83 (m, 1H), 7.69-7.75 (m, 1H), 7.56-7.63 (m, 2H), 7.45 (d, J=6.98 Hz, 1H), 7.38-7.42 (m, 2H), 7.31-7.37 (m, 1H), 2.34 (s, 3H).

Step 11

To 1,8-difluoro-3-(phenylsulfonyl)-7-(o-tolyl)-3,6-dihydropyrrolo[3,2-e]indazole 107-10 (0.300 g, 0.708 mmol) in DMF (10 mL) at 0° C. was added sodium hydride (60% dispersion in oil, 0.056 g, 1.416 mmol) portionwise. The reaction mixture was allowed to attain room temperature and stirred for 15 min. The resulting solution was cooled to 0° C. and 107-3 (0.344 g, 0.919 mmol) was added to it. The reaction mixture was allowed to attain room temperature and stirred for 2 h. After completion of the reaction (monitored by TLC), the reaction mixture was cooled to 0° C. and diluted with water (100 mL). The aqueous layer was separated and extracted with ethyl acetate (2×50 mL). The combined organic layer was washed with water (40 mL) followed by brine (30 mL), dried over anhydrous $Na_2SO_4$, filtered and concentrated under reduced pressure resulting in the crude compound as a brown solid. The resulting crude compound was purified by 100-200 mesh size silica gel column chromatography eluting with 0-30% ethyl acetate in n-hexane to afford 0.300 g (59.1% yield) of 107-11 as a thick brown oil.

LCMS-Condition-1: $[M-Boc]^+$=617.20; Rt=2.579 min $^1$H NMR (400 MHz, DMSO-$d_6$) δ: 7.84-7.92 (m, 1H), 7.74-7.83 (m, 3H), 7.55-7.62 (m, 1H), 7.46 (t, J=7.63 Hz, 2H), 7.12-7.34 (m, 4H), 6.86 (d, J=7.38 Hz, 2H), 6.55 (d, J=5.91 Hz, 2H), 5.09-5.25 (m, 2H), 4.28 (t, J=5.17 Hz, 1H), 4.16 (t, J=5.17 Hz, 1H), 3.88 (q, J=7.38 Hz, 1H), 3.09 (t, J=7.14 Hz, 1H), 2.97 (br. s, 2H), 2.50 (t, J=7.14 Hz, 2H), 1.91 (s, 3H), 1.49-1.68 (m, 2H), 1.18 (br. s, 4H), 1.07 (br. s, 5H).

Step 12

To tert-butyl (4-((1,8-difluoro-3-(phenylsulfonyl)-7-(o-tolyl)pyrrolo[3,2-e]indazol-6(3H)-yl)methyl)phenethyl)(3-fluoropropyl)carbamate 107-11 (0.250 g, 0.348 mmol) in DCM (5 mL) at 0° C. was added trifluoroacetic acid (3 mL) dropwise. The reaction mixture was allowed to attain room temperature and stirred for 2 h. After completion of the reaction (monitored by TLC), the reaction mixture was concentrated under reduced pressure resulting in the crude residue. The crude residue was diluted with DCM (50 mL) and washed with saturated $NaHCO_3$ solution (2×25 mL). The organic layer was separated, dried over anhydrous $Na_2SO_4$, filtered and concentrated under reduced pressure resulting in the crude compound. The resulting crude compound was purified by 100-200 mesh size silica gel column chromatography eluting with 0-8% methanol in DCM to afford 0.150 g (69.7% yield) of 107-12 as a sticky brown oil.

LCMS-Condition-1: $[M+H]^+$=617.00; Rt=1.984 min $^1$H NMR (400 MHz, DMSO-$d_6$) δ: 8.03-8.08 (m, 1H), 7.88-7.99 (m, 3H), 7.69-7.77 (m, 1H), 7.61 (t, J=7.58 Hz, 2H), 7.39-7.47 (m, 2H), 7.29-7.38 (m, 3H), 7.02 (d, J=7.82 Hz, 2H), 6.68 (d, J=7.82 Hz, 2H), 5.25-5.38 (m, 2H), 4.51 (t, J=6.11 Hz, 1H), 4.39 (t, J=5.62 Hz, 1H), 2.66 (d, J=6.85 Hz, 2H), 2.61 (d, J=5.87 Hz, 4H), 2.03 (s, 3H), 1.67-1.82 (m, 2H).

Step 13

To N-(4-((1,8-difluoro-3-(phenylsulfonyl)-7-(o-tolyl)pyrrolo[3,2-e]indazol-6(3H)-yl)methyl)phenethyl)-3-fluoropropan-1-amine 107-12 (0.150 g, 0.243 mmol) in methanol (6 mL) was added aqueous solution of potassium carbonate (0.050 g, 0.362 mmol) at room temperature and stirred for 1 h. After completion of the reaction (monitored by TLC), the reaction mixture was concentrated under reduced pressure, diluted with water (20 mL) and extracted with ethyl acetate (3×20 mL). The combined organic layer was dried over anhydrous $Na_2SO_4$, filtered and concentrated under reduced pressure resulting in the crude compound. The crude compound was purified by Combi Flash column chromatography eluting with 0-10% methanol in DCM to afford 0.010 g (8.6% yield) of D-107 as an off white solid.

LCMS-Condition-1: $[M+H]^+$=477.15; Rt=1.539 min $^1$H NMR (400 MHz, DMSO-$d_6$) δ: 12.63 (br. s, 1H), 7.63 (dd, J=1.47, 9.29 Hz, 1H), 7.29-7.44 (m, 4H), 7.25 (dd, J=1.96, 9.29 Hz, 1H), 7.02 (d, J=7.83 Hz, 2H), 6.68 (d, J=7.83 Hz, 2H), 5.18-5.34 (m, 2H), 4.50 (t, J=5.87 Hz, 1H), 4.39 (t, J=6.11 Hz, 1H), 2.57-2.71 (m, 6H), 2.10 (s, 3H), 1.66-1.82 (m, 3H).

Example 4: Synthesis of 3-Fluoro-N-(3-fluoro-4-((1-fluoro-7-(o-tolyl)pyrrolo[3,2-e]indazol-6(3H)-yl)methyl)phenethyl)propan-1-amine (D-108)

Step 1

To 1-fluoro-3-(phenylsulfonyl)-7-(o-tolyl)-3,6-dihydropyrrolo[3,2-e]indazole (1.00 g, 2.466 mmol) 107-9 in DMF (15 mL) at 0° C. was added sodium hydride (60% dispersion in oil, 0.197 g, 4.932 mmol) portionwise. The reaction mixture was allowed to attain room temperature for 15 min. The resulting solution was cooled to 0° C. and tert-butyl (4-(bromomethyl)-3-fluorophenethyl)(3-fluoropropyl)carbamate 105-5 (1.25 g, 3.187 mmol) was added to it. The reaction mixture was allowed to attain room temperature and stirred for 2 h. After completion of the reaction (monitored by TLC), the reaction mixture was cooled to 0° C. and diluted with water (100 mL). The aqueous layer was separated and extracted with ethyl acetate (2×50 mL). The combined organic layer was washed with water (40 mL) and brine (30 mL), dried over anhydrous $Na_2SO_4$, filtered and concentrated under reduced pressure resulting in the crude compound as a brown solid. The resulting crude compound was purified by 100-200 mesh size silica gel column chromatography eluting with 0-30% ethyl acetate in n-hexane to afford 1.00 g (56.8% yield) of 108-1 as a thick brown oil.

LCMS-Condition-1: $[M+Na]^+$=739.10; Rt=2.520 min

Step 2

To tert-butyl (3-fluoro-4-((1-fluoro-3-(phenylsulfonyl)-7-(o-tolyl)pyrrolo[3,2-e]indazol-6(3H)-yl)methyl)phenethyl)(3-fluoropropyl)carbamate 108-1 (1.00 g, 1.395 mmol) in methanol (15 mL) was added potassium carbonate (0.385 g, 2.789 mmol) at room temperature. The reaction mixture was further heated at 50° C. for 2 h. After completion of the reaction (monitored by TLC), the reaction mixture was concentrated under reduced pressure, diluted with water (100 mL) and extracted with ethyl acetate (2×100 mL). The combined organic layer was washed with water (2×40 mL) and brine (40 mL), dried over anhydrous $Na_2SO_4$, filtered and concentrated under reduced pressure resulting in the crude compound. The resulting crude compound was purified by 100-200 mesh size silica gel column chromatography eluting with 0-5% methanol in DCM to afford 0.700 g (87.0% yield) of 108-2 as a brown semisolid.

LCMS-Condition-1: $[M+Na]^+$=599.10; Rt=2.426 min

Step 3

To 3-fluoro-N-(3-fluoro-4-((1-fluoro-3-(phenylsulfonyl)-7-(o-tolyl)pyrrolo[3,2-e]indazol-6(3H)-yl)methyl)phenethyl)propan-1-amine 108-2 (0.700 g, 1.213 mmol) in DCM (15 mL) at 0° C. was added trifluoroacetic acid (5 mL) dropwise. The reaction mixture was allowed to attain room temperature and stirred for 2 h. After completion of the reaction (monitored by TLC), the reaction mixture was concentrated under reduced pressure resulting in the crude residue. The crude residue was diluted with DCM (mL) and extracted with saturated $NaHCO_3$ solution. The organic layer was separated, dried over anhydrous $Na_2SO_4$, filtered and concentrated under reduced pressure resulting in the crude compound as a brown solid. The resulting crude compound was purified by silica gel column chromatography eluting with 0-8% methanol in DCM, followed by repurification using preparative HPLC to afford 0.105 g (18.1% yield) of D-108 as pale yellow solid.

LCMS-Condition-1: $[M+H]^+$=477.10; Rt=1.581 min $^1$H NMR (400 MHz, DMSO-$d_6$) δ: 8.34 (br. s, 1H), 7.53 (d, J=8.98 Hz, 1H), 7.32 (br. s, 2H), 7.15-7.26 (m, 3H), 6.97 (d, J=10.97 Hz, 1H), 6.81 (d, J=7.98 Hz, 1H), 6.66 (s, 1H), 6.28 (t, J=7.73 Hz, 1H), 5.28 (br. s, 2H), 4.51 (t, J=5.24 Hz, 1H), 4.39 (t, J=5.24 Hz, 1H), 2.88-2.95 (m, 2H), 2.84 (t, J=6.98 Hz, 2H), 2.68-2.77 (m, 2H), 2.06 (s, 3H), 1.78-1.93 (m, 3H).

Example 5: Synthesis of N-(4-((8-Chloro-7-(o-tolyl)pyrrolo[3,2-e]indazol-6(3H)-yl)methyl)phenethyl)-3-fluoropropan-1-amine (D-109)

Step 1

To a solution of 3-(phenylsulfonyl)-7-(o-tolyl)-3,6-dihydropyrrolo[3,2-e]indazole 85-6 (1.00 g, 2.582 mmol) in DCM (15 mL) at 0° C. was added NCS (0.689 g, 5.159 mmol) portionwise. The reaction mixture was allowed to attain room temperature and stirred for 16 h. After completion of the reaction (monitored by TLC), the solid precipitated was filtered and washed with DCM (10 mL) and dried to afford 0.900 g (83.3% yield) of 109-1 as an off white solid.

LCMS-Condition-1: $[M+H]^+$=421.90; Rt=2.634 min $^1$H NMR (400 MHz, DMSO-$d_6$) δ: 12.25 (s, 1H), 8.80 (s, 1H), 8.01 (d, J=8.80 Hz, 1H), 7.90 (d, J=7.82 Hz, 2H), 7.66-7.75 (m, 2H), 7.58 (t, J=7.58 Hz, 2H), 7.31-7.45 (m, 4H), 2.26 (s, 3H).

Step 2

To a solution of 8-chloro-3-(phenylsulfonyl)-7-(o-tolyl)-3,6-dihydropyrrolo[3,2-e]indazole 109-1 (0.900 g, 2.133 mmol) in DMF (20 mL) at 0° C. was added sodium hydride (60% dispersion in oil, 0.170 g, 4.266 mmol) portionwise. The reaction mixture was allowed to attain room temperature and stirred for 15 min. The resulting solution was cooled to 0° C. and tert-butyl (4-(bromomethyl)phenethyl)(3-fluoropropyl)carbamate 107-3 (1.03 g, 2.775 mmol) was added to it. The reaction mixture was allowed to attain room temperature and stirred for 2 h. After completion of the reaction (monitored by TLC), the reaction mixture was cooled to 0° C. and diluted with water (100 mL). The aqueous layer was separated and extracted with ethyl acetate (2×50 mL). The combined organic layer was washed with water (40 mL) followed by brine (30 mL), dried over anhydrous $Na_2SO_4$, filtered and concentrated under reduced pressure. The resulting crude compound was purified by 100-200 mesh size silica gel column chromatography eluting with 0-30% ethyl acetate in n-hexane to afford 1.30 g (85.5% yield) of the title compound 109-2 as a thick brown oil.

LCMS-Condition-1: $[M-Boc]^+$=615.20; Rt=2.581 min

Step 3

To tert-butyl (4-((8-chloro-3-(phenylsulfonyl)-7-(o-tolyl)pyrrolo[3,2-e]indazol-6(3H)-yl)methyl)phenethyl)(3-fluoropropyl)carbamate 109-2 (1.30 g, 1.817 mmol) in DCM (20 mL) at 0° C. was added trifluoroacetic acid (5 mL) dropwise. The reaction mixture was allowed to attain room temperature and stirred for 2 h. After completion of the reaction (monitored by TLC), the reaction mixture was concentrated under reduced pressure resulting in the crude residue. The crude residue was diluted with DCM (50 mL) and washed with saturated $NaHCO_3$ solution (2×25 mL). The organic layer was separated, dried over anhydrous $Na_2SO_4$, filtered and concentrated under reduced pressure resulting in the crude compound. The resulting crude compound was purified by 100-200 mesh size silica gel column chromatography eluting with 0-8% methanol in DCM to afford 0.700 g (63.0% yield) of the title compound 109-3 as brown sticky oil.

LCMS-Condition-1: $[M+H]^+$=615.10; Rt=1.200 min $^1$H NMR (400 MHz, DMSO-$d_6$) δ: 8.82 (s, 1H), 7.99-8.04 (m, 1H), 7.90-7.94 (m, 2H), 7.68-7.74 (m, 1H), 7.59 (t, J=7.67 Hz, 2H), 7.28-7.47 (m, 5H), 7.04 (d, J=7.89 Hz, 2H), 6.71 (d, J=7.89 Hz, 2H), 5.21-5.37 (m, 3H), 4.52 (t, J=5.70 Hz, 1H), 4.40 (t, J=5.48 Hz, 1H), 2.74-2.79 (m, 1H), 2.65 (d, J=6.58 Hz, 4H), 1.96 (s, 3H), 1.68-1.86 (m, 3H).

Step 4

To N-(4-((8-chloro-3-(phenylsulfonyl)-7-(o-tolyl)pyrrolo[3,2-e]indazol-6(3H)-yl)methyl)phenethyl)-3-fluoropropan-1-amine 109-3 (0.700 g, 1.137 mmol) in methanol (25 mL) was added aqueous solution of potassium carbonate (0.314 g, 2.275 mmol) at room temperature and stirred for 1 h. The reaction mixture was further heated at 45° C. for 1 h. After completion of the reaction (monitored by TLC), the reaction mixture was concentrated under reduced pressure, diluted with water (20 mL) and extracted with ethyl acetate (3×20 mL). The combined organic layer was washed with water (2×25 mL) followed by brine (25 mL), dried over anhydrous $Na_2SO_4$, filtered and concentrated under reduced pressure resulting in the crude compound. The crude compound was purified by preparative HPLC purification to afford 0.015 g (3.3% yield) of D-109 as an off white solid.

LCMS-Condition-1: $[M+H]^+$=475.15; Rt=1.587 min $^1$H NMR (400 MHz, DMSO-$d_6$) δ: 13.08 (br. s, 1H), 8.17 (s, 1H), 8.11 (s, 1H), 7.41 (d, J=8.98 Hz, 1H), 7.21-7.31 (m, 3H), 7.18 (d, J=3.49 Hz, 2H), 6.90 (d, J=6.98 Hz, 2H), 6.58 (d, J=7.98 Hz, 2H), 4.99-5.20 (m, 2H), 4.37 (t, J=5.73 Hz, 1H), 4.25 (t, J=5.73 Hz, 1H), 2.53-2.62 (m, 2H), 2.44-2.53 (m, 4H), 1.88 (s, 3H), 1.54-1.70 (m, 2H).

Activity and Biological Data

In order to demonstrate the utility of the compounds of this invention, an estrogen receptor binding assay was performed wherein many of the compounds of this invention were shown to demonstrate significant affinity for the estrogen receptor. Selected compound examples were assessed for their ability to inhibit estradiol (E2)-induced proliferation and signaling and for their ability to degrade the estrogen receptor (ER) in breast cancer cells. Furthermore, the ability of selected compounds to inhibit E2-induced increase in uterine weight in immature rats was assessed by oral dosing. Selected compounds could be evaluated in an MCF-7 in vivo xenograft model of breast cancer.

Proliferation Assay in MCF-7 and T47 D Cells

MCF-7 and T47D cells were stripped for 3 days in phenol red-free RPMI1640 media containing 10% charcoal-stripped fetal bovine serum (CS-FBS) and 1% Penicillin/streptomycin (P/S). Cells (volume of 90 μl/well) were seeded in 96 well plates at a density of 2500 cells/well for MCF-7 cells and 1500 cells/well for T47D cells. On the following day, plates were treated with the test compounds (10× concentration in media, volume of 10 μl/well added) both in the absence and in the presence of two doses of E2 (10 pM and 1 nM). The cells were incubated with test compounds for 7 days. The viability of the cells was assessed using CellTiterGlo (Promega, Cat #G7573) according to the manufacturer's instructions. Growth inhibition curves and $IC_{50}$ values were calculated using the GraphPad-Prism 6.0 software. Data values shown in Table 1 were obtained using the 10 pM dose of E2.

Quantitative PCR (gPCR) to Assess ER Signaling in MCF-7 Cells

MCF-7 cells were stripped for 3 days in phenol red-free RPMI1640 media containing 10% charcoal-stripped fetal bovine serum (CS-FBS) and 1% Penicillin/streptomycin (P/S). Cells (volume of 90 μl/well) were seeded in 96 well plates at a density of 20000 cells/well. On the following day, plates were treated with the test compounds (10× concentration in media, volume of 10 μl/well added) both in the absence and in the presence of E2 (1 nM). The cells were incubated with test compounds for 24 h. Cell lysates were prepared using the Cells-to-CT kit (ThermoFisherScientific, Cat #A25603) according to the manufacturer's instructions. A PCR mix containing master mix, primers for progesterone receptor (PR) and glyceraldehyde-3-phosphate dehydrogenase (GAPDH) endogenous control (ThermoFisherScientific, PR: Cat #Hs01556702_m1 and GAPDH: 4326317E), RNase free water (ThermoFisherScientific, Cat #AM9938) was prepared and 8 μl of this mix was added to each well of a MicroAmp Optical 384-well plate. Cell lysates (2 μl) were then added to the respective wells and samples were analyzed using the QuantStudio6 machine using the fast cycling conditions provided in the kit. Inhibition of PR induction was analyzed and IC50 values were calculated using the GraphPadPrism 6.0 software. In general, the activity in this assay tracked similarly to the MCF-7 inhibition data shown in Table 1. Many of the compounds of the invention potently suppressed PR induction when stimulated by 1 nM E2.

ER Degradation Assay in MCF-7 Cells

MCF-7 cells were stripped for 3 days in phenol red-free RPMI1640 media containing 10% charcoal-stripped fetal bovine serum (CS-FBS) and 1% Penicillin/streptomycin (P/S). Cells were seeded in 6 well plates at a density of 4x10≡cells/well (volume of 2 ml/well). On the following day, plates were treated with the test compounds (3× concentration in media, volume of 1 ml/well added). The cells were incubated with test compounds for 48 h. Cells were washed and lysed using 70 µl/well of CelLyticM (Sigma, Cat #C2978) lysis buffer containing protease and phosphatase inhibitors at room temperature for 15 minutes. The lysates were centrifuged at 15000 rpm for 15 mins and the supernatant was collected and concentration were analyzed using the Bicinchoninic acid assay (BCA). Proteins (25 µg) were loaded and separated on a 4-15% polyacrylamide gel. Proteins were then transferred to a PVDF membrane and the membranes were then incubated with the ERα primary antibody (Cell Signaling, Cat #13258; 1:1000) and the vinculin primary antibody (Sigma, Cat #V9131, 1:1000). Membranes were incubated with the respective secondary antibodies, probed with chemiluminescent substrates (ThermoFisherScientific, Dura (ERα): Cat #34075 and Pico (Vinculin): Cat #34080), and images were captured using the Azure Biosystems c600 machine. Images were analyzed using the AzureSpot software. Several tested compounds disclosed herein decreased expression of the ER.

Immature Rat Uterine Assay

Sprague-Dawley rat pups were weaned at 19 days of age, randomized into groups (n=6), and administered vehicle (aqueous 20% HPBCD, 10% PEG400 in $H_2O$), E2 (0.01 mg/kg), test compounds (0.1 mg/kg-3 mg/kg) in combination with E2 (0.01 mg/kg), either by subcutaneous injection or by oral gavage, once daily for three consecutive days. Twenty-four hours after the final dose, all animals were killed by carbon dioxide inhalation. Body weights and wet uterine weights were recorded for each animal. GraphPad-Prism 6.0 software was used to analyze data. For example, compound D-105 suppressed wet uterine weight to baseline with an oral dose of 3 mg/kg.

MCF-7 Xenograft Models

Female athymic nude mice [Crl:NU(NCr)-Foxn1nu] are used for tumor xenograft studies. Three days before tumor cell implantation, estrogen pellets (0.36 mg E2, 60-day release; Innovative Research of America, Sarasota, Florida, USA) are implanted subcutaneously between the scapulae of test animals with a sterilized trochar. MCF-7 human breast adenocarcinoma cells are cultured to midlog phase in RPMI-1640 medium containing 10% fetal bovine serum, 100 U/ml penicillin G, 100 µg/ml streptomycin sulfate, 2 mmol/l glutamine, 10 mmol/l HEPES, 0.075% sodium bicarbonate, and 25 µg/ml gentamicin. On the day of tumor cell implantation, the cells are trypsinized, pelleted, and resuspended in PBS at a concentration of 5x107 cells/ml. Each test mouse receives $1\times10^7$ MCF-7 cells implanted subcutaneously in the right flank, and tumor growth is monitored. Volume is calculated using the following formula: tumor volume ($mm^3$)=lxw2/2, where w=width and 1=length in mm of an MCF-7 tumor. When necessary, tumor weight is estimated on the basis of the assumption that 1 $mm^3$ of tumor volume is equivalent to 1 mg tumor wet weight. Fourteen days after tumor cell implantation (designated as day 1 of the study), mice are 9 weeks of age, with body weights ranging from 21.4 to 32.5 g, individual tumor volumes ranging from 75 to 144 $mm^3$, and a group mean tumor volume (MTV) of 108 $mm^3$. The mice are randomized into groups of 9-15 animals each and treated with vehicle, control SERM such as tamoxifen (1 mg/animal every other day), and test compound (0.3, 1, 3, 10, 30, 60, 90, and 120 mg/kg daily). Tumor volumes are evaluated twice per week. The tumor endpoint is defined as an MTV of 1500 $mm^3$ in the control group. Animals are also monitored for partial regression (PR) and complete regression responses. Treatment tolerability is assessed by body weight measurements and frequent observation for clinical signs of treatment-related adverse effects. Animals with weight loss exceeding 30% for one measurement, or exceeding 25% for three measurements, are humanely sacrificed and their deaths are classified as treatment-related deaths. Acceptable toxicity is defined as a group mean body weight loss of less than 20% during the study and not more than one treatment-related death among 10 treated animals, or 10%. At the end of the study, the animals are sacrificed by terminal cardiac puncture under isoflurane anesthesia.

TABLE 1

MCF-7 Proliferation Inhibition Assay

| Compound | $IC_{50}$ |
|---|---|
| D-105 | +++ |
| D-106 | +++ |
| D-107 | +++ |
| D-108 | +++ |
| D-109 | +++ |
| D-110 | na |

+++ $IC_{50}$ < 1 nM;
++ $IC_{50}$ > 1 nM < 10 nM;
+ $IC_{50}$ > 10 nM;
na = data not available

What is claimed is:

1. A compound having a structure selected form the group consisting of:

D-105

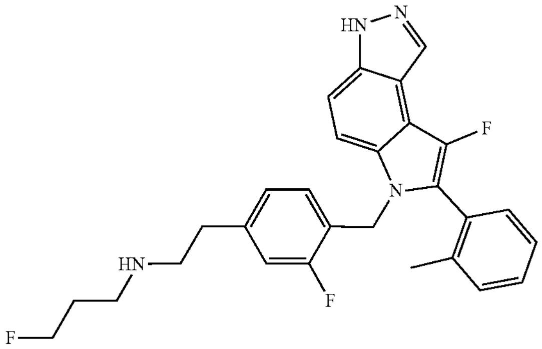

,

-continued
D-106
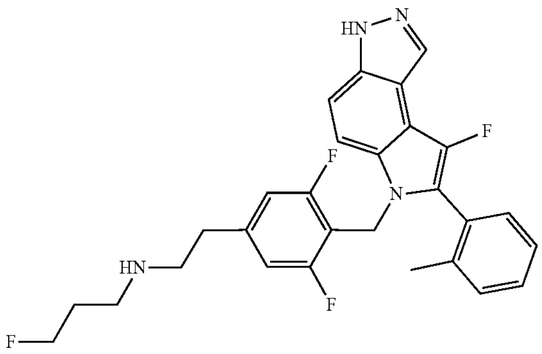
,
D-107
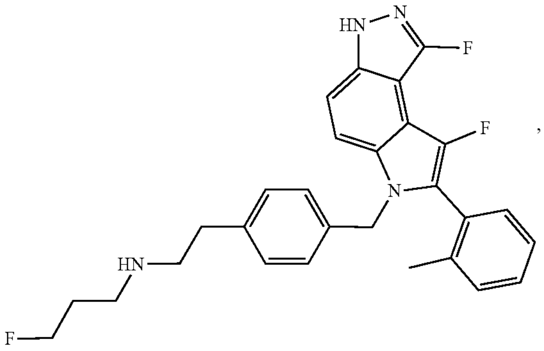
,
D-108
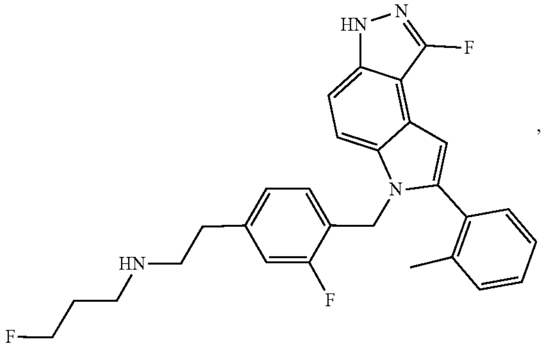
,
D-109
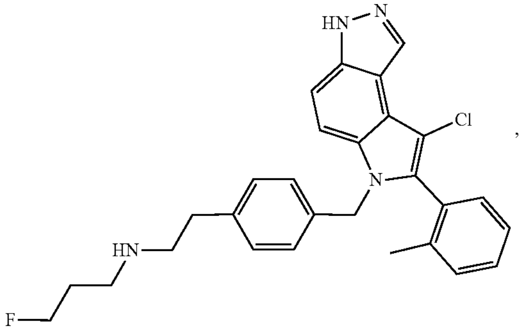
, and
-continued
D-110
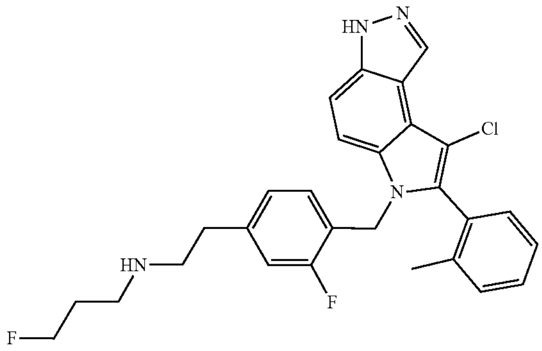
;
or a pharmaceutically acceptable salt thereof.
2. The compound of claim 1, having a structure according to Formula D-105:
D-105
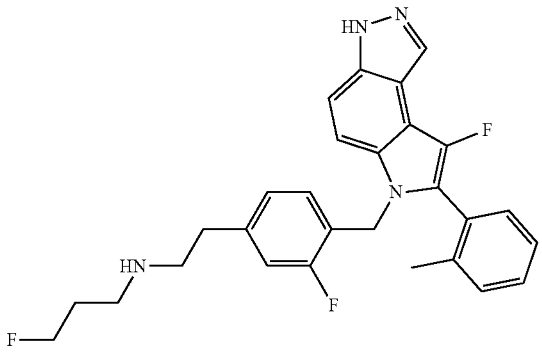
;
or a pharmaceutically acceptable salt thereof.
3. The compound of claim 1, having a structure according to Formula D-106:
D-106
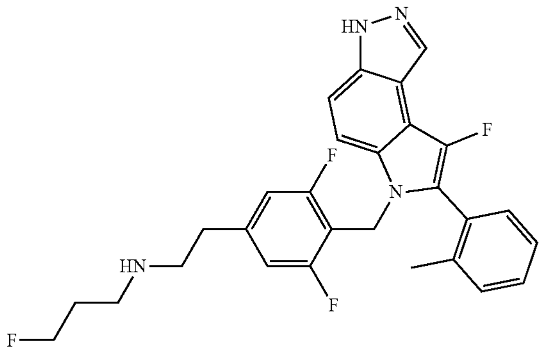
;
or a pharmaceutically acceptable salt thereof.

4. The compound of claim 1, having a structure according to Formula D-107:

D-107

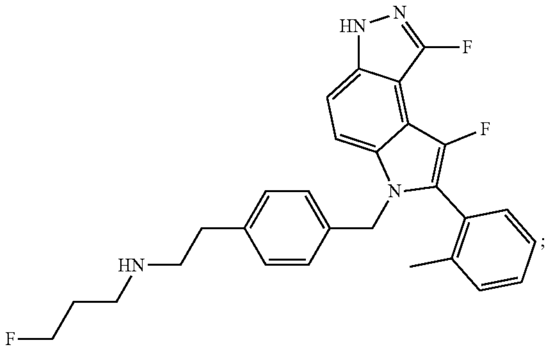

or a pharmaceutically acceptable salt thereof.

5. The compound of claim 1, having a structure according to Formula D-108:

D-108

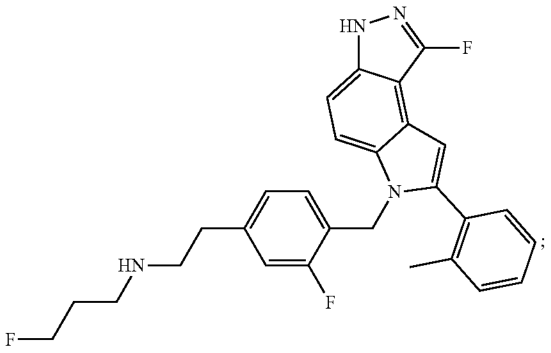

or a pharmaceutically acceptable salt thereof.

6. The compound of claim 1, having a structure according to Formula D-109:

D-109

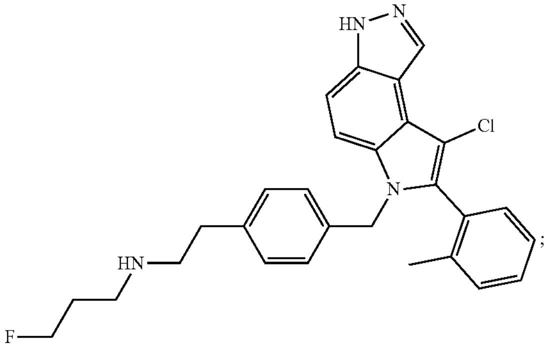

or a pharmaceutically acceptable salt thereof.

7. The compound of claim 1, having a structure according to Formula D-110:

D-110

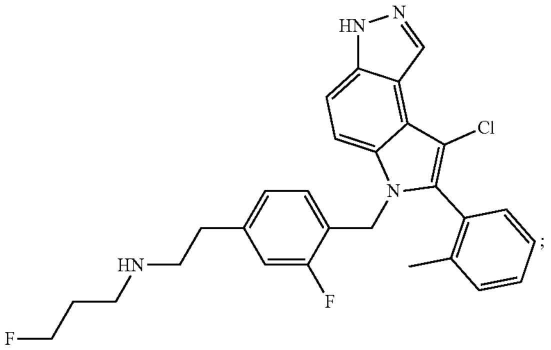

or a pharmaceutically acceptable salt thereof.

8. A pharmaceutical composition comprising a compound of claim 1, and a pharmaceutically acceptable excipient.

9. A method of treating a disease, syndrome, illness, or symptom associated with insufficient or overabundant estrogen levels in a mammal in need thereof, comprising administering to said mammal an effective amount of a compound of claim 1, or a pharmaceutically acceptable salt thereof.

10. A method of treating a cancer selected from the group consisting of prostate cancer, breast cancer, endometrial cancer, lung cancer, hepatocellular cancer, lymphoma, multiple endocrine neoplasia, vaginal cancer, renal cancer, thyroid cancer, testicular cancer, leukemia, and ovarian cancer in a mammal in need thereof, comprising administering to said mammal an effective amount of a compound of claim 1, or a pharmaceutically acceptable salt thereof.

* * * * *